US012721964B2

(12) United States Patent
(10) Patent No.: US 12,721,964 B2
(45) Date of Patent: Sep. 1, 2026

Ohtsuki et al.

(54) INFORMATION PROCESSING DEVICE, INFORMATION PROCESSING METHOD, PROGRAM, AND DATA CONFIGURATION

(71) Applicant: DENSO TEN Limited, Kobe (JP)

(72) Inventors: Tomoe Ohtsuki, Kobe (JP); Hiroyuki Watabe, Kobe (JP); Shinichi Shiotsu, Kobe (JP); Motoki Kojima, Kobe (JP); Minoru Maehata, Kobe (JP); Miki Hitotsuya, Kobe (JP); Haruo Harada, Kobe (JP)

(73) Assignee: DENSO TEN Limited, Kobe (JP)

( * ) Notice: Subject to any disclaimer, the term of this patent is extended or adjusted under 35 U.S.C. 154(b) by 800 days.

(21) Appl. No.: 18/026,324

(22) PCT Filed: Mar. 9, 2021

(86) PCT No.: PCT/JP2021/009159

§ 371 (c)(1),
(2) Date: Mar. 14, 2023

(87) PCT Pub. No.: WO2022/113386

PCT Pub. Date: Jun. 2, 2022

(65) Prior Publication Data

US 2023/0355919 A1 Nov. 9, 2023

(30) Foreign Application Priority Data

Nov. 30, 2020 (JP) ................................ 2020-199145
Nov. 30, 2020 (JP) ................................ 2020-199148
Nov. 30, 2020 (JP) ................................ 2020-199149

(51) Int. Cl.
*A61M 21/02* (2006.01)
*B60K 35/22* (2024.01)
(Continued)

(52) U.S. Cl.
CPC ............ *A61M 21/02* (2013.01); *B60K 35/22* (2024.01); *B60K 35/26* (2024.01); *B60K 35/60* (2024.01);
(Continued)

(58) Field of Classification Search
None
See application file for complete search history.

(56) References Cited

U.S. PATENT DOCUMENTS

2009/0002142 A1* 1/2009 Morimoto ............. H04N 9/641 340/425.5
2011/0255842 A1 10/2011 Hindle et al.
(Continued)

FOREIGN PATENT DOCUMENTS

DE 10 2015 011 708 A1 5/2016
DE 10 2016 215 251 A1 2/2018
(Continued)

OTHER PUBLICATIONS

Nakamura et al., "Examination of TV chat robot for the purpose of preventing motion sickness during autonomous driving," IEICE Technical Report, The Institute of Electronics, Information and Communication Engineers, Feb. 12, 2018, vol. 117, No. 442, pp. 133-138.
(Continued)

*Primary Examiner* — Krishna P Neupane
(74) *Attorney, Agent, or Firm* — Oliff PLC

(57) ABSTRACT

A problem to be solved is to restrict sickness of a user due to a digital content that includes virtual space experience. In order to solve the above-mentioned problem, an information processing device according to one aspect of embodiments includes an acquisition unit, an estimation unit, and a restraint processing unit. The acquisition unit acquires a state inside and outside related to a user of a digital content
(Continued)

that includes virtual space experience. The estimation unit estimates a state of sickness of the user based on a state that is acquired by the acquisition unit. The restraint processing unit executes a restraining process of sickness related to a sound of the digital content in accordance with the state of sickness of the user that is estimated by the estimation unit.

18 Claims, 15 Drawing Sheets

(51) Int. Cl.

| | |
|---|---|
| ***B60K 35/26*** | (2024.01) |
| ***B60K 35/60*** | (2024.01) |
| ***B60K 35/65*** | (2024.01) |
| ***B60K 35/80*** | (2024.01) |
| ***G06F 3/01*** | (2006.01) |
| *A61M 21/00* | (2006.01) |

(52) U.S. Cl.

CPC ............ *B60K 35/656* (2024.01); *B60K 35/80* (2024.01); *G06F 3/013* (2013.01); *A61M 2021/0027* (2013.01); *G06F 2203/011* (2013.01)

(56) References Cited

U.S. PATENT DOCUMENTS

| | | | | |
|---|---|---|---|---|
| 2017/0345212 | A1* | 11/2017 | Palmieri et al. | B60K 35/26 |
| 2018/0089900 | A1 | 3/2018 | Rober et al. | |
| 2018/0296921 | A1* | 10/2018 | Watson | A63F 13/54 |
| 2019/0022347 | A1 | 1/2019 | Wan et al. | |
| 2019/0365321 | A1 | 12/2019 | Son | |
| 2020/0383580 | A1* | 12/2020 | Shouldice | A61B 5/0205 |
| 2022/0001893 | A1 | 1/2022 | Tartz | |

FOREIGN PATENT DOCUMENTS

| | | | |
|---|---|---|---|
| DE | 10 2018 206 657 | A1 | 10/2019 |
| DE | 10 2019 003 429 | A1 | 11/2020 |
| DE | 10 2019 112 292 | A1 | 11/2020 |
| DE | 10 2019 208 970 | A1 | 12/2020 |
| JP | 2009-135686 | A | 6/2009 |
| JP | 2010-083276 | A | 4/2010 |
| JP | 2010-105643 | A | 5/2010 |
| JP | 6092437 | B1 | 3/2017 |
| JP | 2017-102401 | A | 6/2017 |
| JP | 2017-116995 | A | 6/2017 |
| JP | 2018-514005 | A | 5/2018 |
| JP | 2018-126185 | A | 8/2018 |
| JP | 2020-018770 | A | 2/2020 |
| KR | 10-2020-0144202 | A | 12/2020 |
| WO | 2019/177002 | A1 | 9/2019 |

OTHER PUBLICATIONS

Jun. 15, 2021 International Search Report issued in International Patent Application No. PCT/JP2021/009159.

* cited by examiner

FIG.5

| RESTRAINING PROCESS | DETAILS |
|---|---|
| REDUCING PROCESS OF SOUND IMAGE LOCALIZATION FEELING | MIX NON-LOCALIZED SOUND |
| | MIX SOUND WHOSE LOCALIZATION HAS NO CORRELATION WITH IMAGE |
| | EXECUTE SOUND LOCALIZING PROCESS; HOWEVER, DOES NOT ALLOW MOVING PROCESS THEREOF |
| | SHORTEN LOCALIZATION MOVEMENT DISTANCE |
| | OUTPUT LEFT AND RIGHT SOUNDS IN ANTIPHASE |
| | EMPHASIZE AND SYNTHESIZE DEEP BASS SOUND |
| | OUTPUT HEALING SOUND OR ENVIRONMENTAL SOUND |
| | SYNTHESIZE SOUND OF BGM AT LARGE RATIO |
| | SWITCH SOUND SENSING SOURCE |
| REDUCING PROCESS OF SOUND-VOLUME CHANGING SPEED | - |
| RESTRICTING PROCESS OF VOLUME CHANGING WIDTH | - |

FIG.6

HARDLY GET SICKNESS← →EASILY GET SICKNESS

| | | CONTENT TYPE | | | | | |
|---|---|---|---|---|---|---|---|
| | | A | | B | | C | |
| DEGREE OF SICKNESS | L1 | SOUND | - | SOUND | - | SOUND | PROCESS a |
| | | IMAGE | - | IMAGE | PROCESS l | IMAGE | PROCESS m |
| | L2 | SOUND | - | SOUND | PROCESS a | SOUND | PROCESS b |
| | | IMAGE | PROCESS l | IMAGE | PROCESS m | IMAGE | PROCESS n |
| | L3 | SOUND | PROCESS a | SOUND | PROCESS b | SOUND | PROCESS c |
| | | IMAGE | PROCESS m | IMAGE | PROCESS n | IMAGE | PROCESS o |

→SMALL

LARGE←

FIG.10

| PROCESSING DETAILS | DETAILS |
|---|---|
| BALANCE ADJUSTMENT ACCORDING TO DEGREE OF VR SICKNESS | LIGHT VR SICKNESS →INDEPENDENTLY EXECUTE RESTRAINING PROCESS RELATED TO SOUND |
| | MIDDLE VR SICKNESS →INDEPENDENTLY EXECUTE RESTRAINING PROCESS RELATED TO IMAGE |
| | EXECUTE RESTRAINING PROCESS RELATED TO EACH OF SOUND AND IMAGE AT CORRESPONDING INTENSITY THAT IS DECIDED IN ACCORDANCE WITH EXTENT |
| BALANCE ADJUSTMENT RELATED TO SOUND | NOT SIMPLY ADD SOUNDS TO EACH OTHER, BUT SYNTHESIZE SOUNDS WITH EACH OTHER IN ACCORDANCE WITH ENVIRONMENT |

FIG.11

HARDLY GET SICKNESS← →EASILY GET SICKNESS

| DEGREE OF SICKNESS (→LOW / HIGH←) | | CONTENT TYPE A | | CONTENT TYPE B | | CONTENT TYPE C | |
|---|---|---|---|---|---|---|---|
| | L1 | SOUND | PROCESS a1 | SOUND | PROCESS a2 | SOUND | PROCESS a3 |
| | | IMAGE | - | IMAGE | PROCESS l2 | IMAGE | PROCESS l3 |
| | L2 | SOUND | PROCESS b1 | SOUND | PROCESS b2 | SOUND | PROCESS b3 |
| | | IMAGE | PROCESS m1 | IMAGE | PROCESS m2 | IMAGE | PROCESS m3 |
| | L3 | SOUND | PROCESS c1 | SOUND | PROCESS c2 | SOUND | PROCESS c3 |
| | | IMAGE | PROCESS n1 | IMAGE | PROCESS n2 | IMAGE | PROCESS n3 |

START

S201 ACQUIRE STATE INSIDE AND OUTSIDE RELATED TO USER

S202 ESTIMATE STATE OF VR SICKNESS

S203 ADJUST BALANCE BETWEEN RESTRAINING PROCESSES OF VR SICKNESS RELATED TO SOUND AND IMAGE IN ACCORDANCE WITH ESTIMATION RESULT

S204 EXECUTE RESTRAINING PROCESS AT ADJUSTED BALANCE

END

1B

10B
INFORMATION PROCESSING DEVICE

12
CONTROL UNIT

11
STORAGE

3
HMD

12a
PROVISION UNIT

11a
VR CONTENT DB

5
VARIOUS SENSORS

12b
ACQUISITION UNIT

11b
USER INFORMATION

5a
CAMERA

12c
ESTIMATION UNIT

11c
ESTIMATION MODEL

5b
VITAL SENSOR

12d
RESTRAINT PROCESSING UNIT

11d
RESTRAINING PROCESS INFORMATION

5c
ACCELERATION SENSOR

11e
GUIDANCE INFORMATION DB

5d
STEERING-ANGLE SENSOR

| PROCESSING DETAILS |
| --- |
| GUIDE GAZE OF USER |
| URGE TO TAKE POSTURE FOR HARDLY GETTING SICKNESS |
| OUTPUT ALARM SOUND WITH RESPECT TO ESTIMATED BEHAVIOR OF VEHICLE |
| URGE USER TO UTTER |
| INDUCE DROWSINESS OF USER |
| GUIDE BY USING VIBRATION |

FIG.17

HARDLY GET SICKNESS← →EASILY GET SICKNESS

| | | | | | | | |
|---|---|---|---|---|---|---|---|
| | | CONTENT TYPE | | | | | |
| | | A | | B | | C | |
| →LOW | L1 | SOUND | GUIDANCE SOUND a1 | SOUND | GUIDANCE SOUND a2 | SOUND | GUIDANCE SOUND a3 |
| | | IMAGE | - | IMAGE | PROCESS l | IMAGE | PROCESS m |
| DEGREE OF SICKNESS | L2 | SOUND | GUIDANCE SOUND b1 | SOUND | GUIDANCE SOUND b2 | SOUND | GUIDANCE SOUND b3 |
| | | IMAGE | PROCESS l | IMAGE | PROCESS m | IMAGE | PROCESS n |
| | L3 | SOUND | GUIDANCE SOUND c1 | SOUND | GUIDANCE SOUND c2 | SOUND | GUIDANCE SOUND c3 |
| HIGH← | | IMAGE | PROCESS m | IMAGE | PROCESS n | IMAGE | PROCESS o |

INFORMATION PROCESSING DEVICE, INFORMATION PROCESSING METHOD, PROGRAM, AND DATA CONFIGURATION

CROSS-REFERENCE TO RELATED APPLICATIONS

This application is national stage application of International Application No. PCT/JP2021/009159, filed on Mar. 9, 2021, which designates the United States, incorporated herein by reference, and which claims the benefit of priority from Japanese Patent Application Nos. 2020-199145, filed on Nov. 30, 2020, 2020-199148, filed on Nov. 30, 2020, and 2020-199149, filed on Nov. 30, 2020, the entire contents of which are incorporated herein by reference.

FIELD

The embodiments discussed herein are directed to an information processing device, an information processing method, a program, and a data configuration.

BACKGROUND

Conventionally, there has been known a technology for providing a digital content that includes virtual space experience such as Virtual Reality (VR) and Mixed Reality (MR), to a user by using a Head Mounted Display (HMD) and the like.

In the above-mentioned technology, there has been also proposed a VR system that is provided in a moving body such as a vehicle to be capable of using the above-mentioned moving body as a motion platform (see Patent Literature 1, for example).

CITATION LIST

Patent Literature

Japanese Laid-open Patent Publication No. 2017-102401

SUMMARY

Technical Problem

However, the conventional technology has a room for improvement in restricting sickness of a user due to a digital content including virtual space experience.

For example, there has been known that "VR sickness" similar to motion sickness occurs in a user that is receiving provision of a VR content. The VR sickness is one of kinesia to be caused by synchronous deviation between sounds and images, and/or the fact that fluctuation in sounds and images is large and processing of a brain does not catch up with it, for example. Particularly, in a case of a VR system provided in a vehicle, sickness of a user tends to increase because general motion sickness is added thereto.

Solution to Problem

An information processing device according to one aspect of embodiments includes an acquisition unit, an estimation unit, and a restraint processing unit. The acquisition unit acquires a state inside and outside related to a user of a digital content that includes virtual space experience. The estimation unit estimates a state of sickness of the user based on a state that is acquired by the acquisition unit. The restraint processing unit executes a restraining process of sickness related to a sound of the digital content in accordance with the state of sickness of the user that is estimated by the estimation unit.

Advantageous Effects of Invention

BRIEF DESCRIPTION OF DRAWINGS

FIG. 5 is a diagram illustrating processing details of a restraining process according to the first embodiment.

FIG. 6 is a diagram illustrating one example of restraining process information according to the first embodiment.

FIG. 10 is a diagram illustrating processing details of a restraining process according to the second embodiment.

FIG. 11 is a diagram illustrating one example of restraining process information according to the second embodiment.

FIG. 16 is a diagram illustrating processing details of a restraining process according to the third embodiment.

FIG. 17 is a diagram illustrating one example of restraining process information according to the third embodiment.

DESCRIPTION OF EMBODIMENTS

Hereinafter, embodiments of an information processing device, an information processing method, a program, and a data configuration disclosed in the present application will be described in detail with reference to the accompanying drawings. Moreover, the present disclosure is not limited to the embodiments described below.

Hereinafter, cases are exemplified where each of information processing systems 1, 1A, and 1B according to the embodiments is an on-vehicle system provided in a vehicle (V). Hereinafter, each of the information processing systems 1, 1A, and 1B according to the embodiments is explained to be a VR system configured to provide, to a user, a VR content as a digital content that includes virtual space experience.

1. First Embodiment

Figure 1:
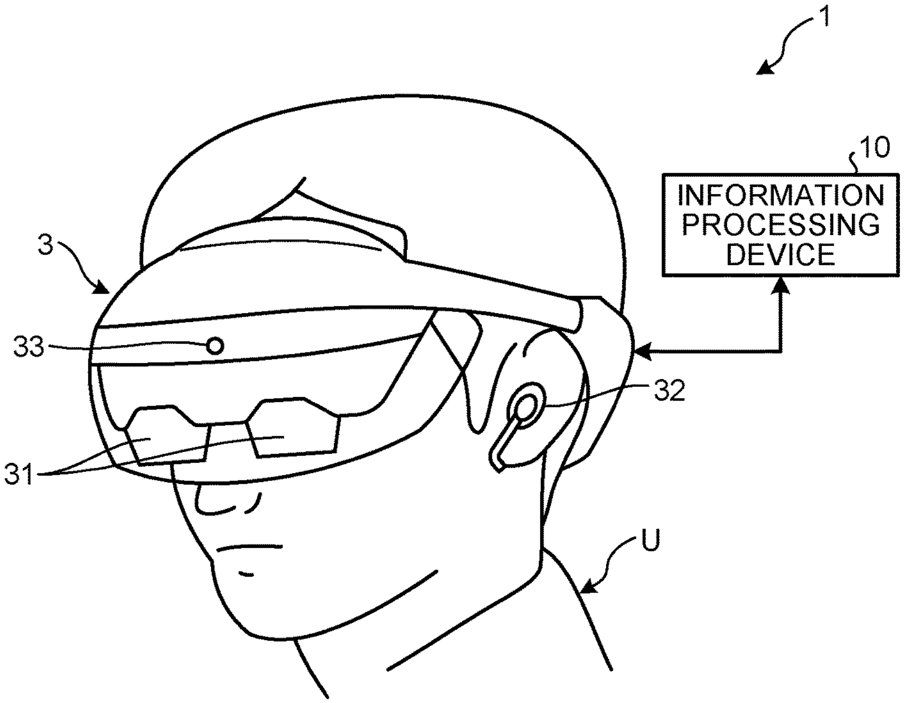
FIG. 1 is a diagram illustrating a schematic configuration of an information processing system according to a first embodiment.
Figure 2:
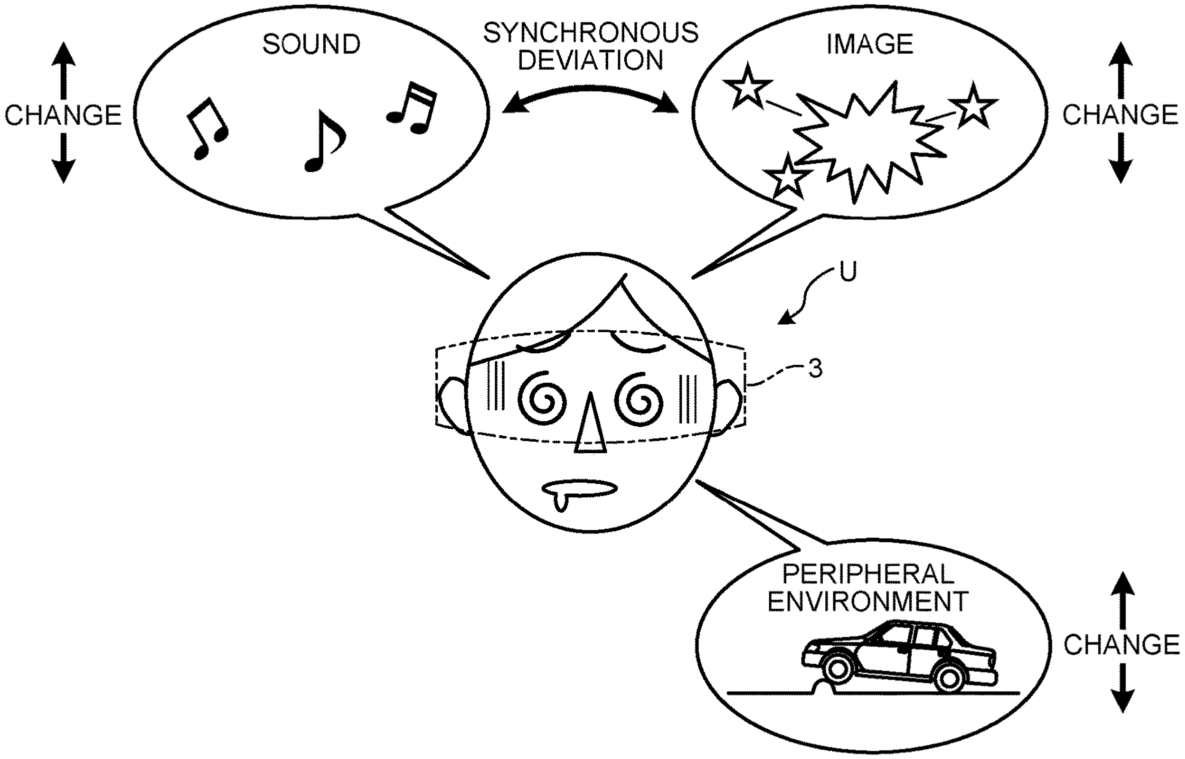
FIG. 2 is a diagram illustrating VR sickness.
Figure 3:
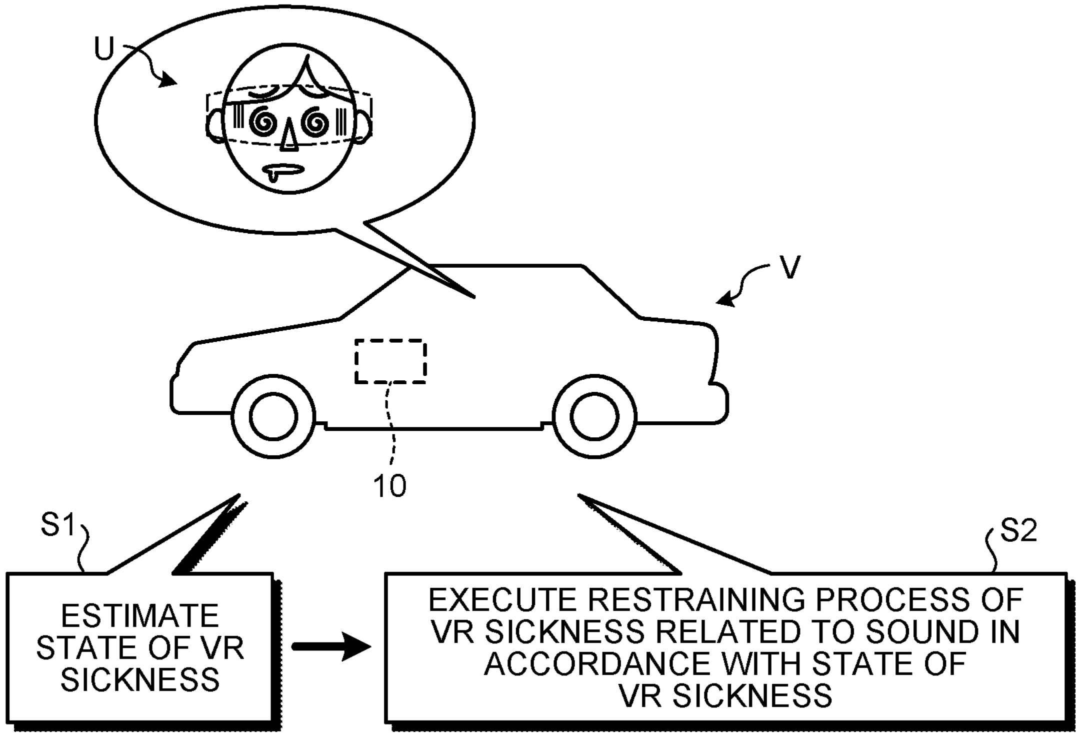
FIG. 3 is a diagram illustrating the outline of an information processing method according to the first embodiment.

The outline of an information processing method according to a first embodiment will be explained with reference to FIG. 1 to FIG. 3. FIG. 1 is a diagram illustrating a schematic configuration of the information processing system 1 according to the first embodiment. FIG. 2 is a diagram illustrating VR sickness. FIG. 3 is a diagram illustrating the outline of an information processing method according to the first embodiment.

As illustrated in FIG. 1, the information processing system 1 according to the first embodiment includes an HMD 3 and an information processing device 10.

The HMD 3 is an information processing terminal that is configured to present a VR content provided by the information processing device 10 to a user U so as to cause the user to enjoy VR experience. The HMD 3 is a wearable computer that is attached to a head portion of the user U and is used, and in the example illustrated in FIG. 1, the HMD 3 has a goggle-type. Note that the HMD 3 may have an eyeglass-type or a hat-type.

The HMD 3 includes a display 31, a speaker 32, and a sensor unit 33. The display 31 is configured to be arranged before eyes of the user U so as to display an image included in a VR content that is provided by the information processing device 10.

In the example illustrated in FIG. 1, the displays 31 are arranged before respective left and right eyes of the user U; however, the single display 31 may be provided. Moreover, the display 31 may have a nontransparent-type that completely covers an eyesight, or may have a video transmission-type or an optically transmission-type. In the present embodiment, a nontransparent-type is employed.

For example, as illustrated in FIG. 1, the speaker 32 is configured to have a headphone-type to be arranged in an ear of the user U. The speaker 32 outputs a sound that is included in a VR content provided by the information processing device 10.

The sensor unit 33 is a device that is configured to detect change in a state inside and outside of the user U, and further includes, for example, a camera, a sensor, and the like.

The information processing device 10 is a computer, for example, and further is an on-vehicle device that is provided in a vehicle and further is connected to the HMD 3 in a wired or wireless manner so as to provide a VR content to the HMD 3. The information processing device 10 acquires, at any time, change in a state detected by the sensor unit 33 so as to reflect the above-mentioned change in the state on a VR content.

For example, the information processing device 10 is capable of changing a direction of an eyesight in a virtual space of a VR content in accordance with change in a head portion and/or a gaze of the user U, which is detected by the sensor unit 33.

Incidentally, there has been known that "VR sickness" similar to motion sickness can occur in the user U in provision of a VR content with the use of the above-mentioned HMD 3.

As illustrated in FIG. 2, VR sickness is caused by synchronous deviation between sounds and images, and/or the fact that fluctuation in sounds and images is large and processing of a brain does not catch up with it, for example. Moreover, VR sickness can be caused by a gap between a sense by VR experience that is enjoyed by using the HMD 3 and a perceptive sense of the user U him/herself caused by change in a peripheral environment.

Therefore, an information processing method according to the first embodiment includes: acquiring a state inside and outside related to the user U; estimating a state of VR sickness of the user U on the basis of the acquired state; and executing a restraining process of VR sickness related to sounds in accordance with the estimated state of VR sickness.

Specifically, as illustrated in FIG. 3, in the information processing method according to the first embodiment, the information processing device 10 acquires, at any time, a state inside and outside related to the user U, and further estimates a state of VR sickness of the user U (Step S1). For example, the information processing device 10 detects change in a physical state of the user U, and further estimates a state of VR sickness.

For example, the information processing device 10 estimates a state of VR sickness on the basis of a use state of a VR content such as a type, a state of images, and a state of sounds of the VR content during provision.

For example, the information processing device 10 estimates a state of VR sickness on the basis of a traveling state of a vehicle such as a road state, a state of a vehicle, and an operation state. For example, the information processing device 10 estimates a state of VR sickness on the basis of user information that includes various parameters indicating a sickness tendency for each user, etc.

In the above-mentioned estimating process of the state of VR sickness, for example, the information processing device 10 may use an estimation model that is generated by using algorithm of machine learning. Reinforcement learning is appropriately executed on the above-mentioned estimation model on the basis of an estimation result of an actual state of VR sickness. For example, as a result of the reinforcement learning, a determination threshold for estimating a state of VR sickness and the like are appropriately updated.

In accordance with an estimation result in Step S1, the information processing device 10 executes a restraining process of VR sickness related to a sound of a VR content (Step S2). The restraining process of VR sickness related to a sound includes generally weakening stimulation related to a sound of a VR content, and may be a reducing process of sound image localization feeling, for example.

The restraining process of VR sickness related to sounds is a reducing process of a sound-volume changing speed, for example. The restraining process of VR sickness related to sounds is a restricting process of a volume changing width, for example. Note that details of the restraining process of VR sickness related to sounds will be mentioned later with reference to FIG. 5 and the like.

As described above, stimulation related to sounds of a VR content is weakened, so that it is possible to ease sickness that is evoked by at least a sound of the VR content. In other words, it is possible to contribute to restriction on VR sickness of the user U due to a VR content.

In FIG. 3, the restraining process of VR sickness related to sounds is explained to be executed; however, a restraining process of VR sickness related to images may be used in conjunction therewith. The restraining process of VR sickness related to images includes generally weakening stimulation related to images of a VR content, and may be a reducing process of, for example, contrast, a color tone, and the like.

As described above, the information processing method according to the first embodiment includes: acquiring a state inside and outside related to the user U; estimating a state of VR sickness of the user U on the basis of the acquired state; and executing the restraining process of VR sickness related to sounds in accordance with the estimated state of VR sickness.

Therefore, in accordance with the information processing method according to the first embodiment, it is possible to restrict VR sickness of the user U due to a VR content. Hereinafter, a configuration example of the information processing system 1 will be specifically explained, to which the information processing method according to the first embodiment is applied.

Figure 4:
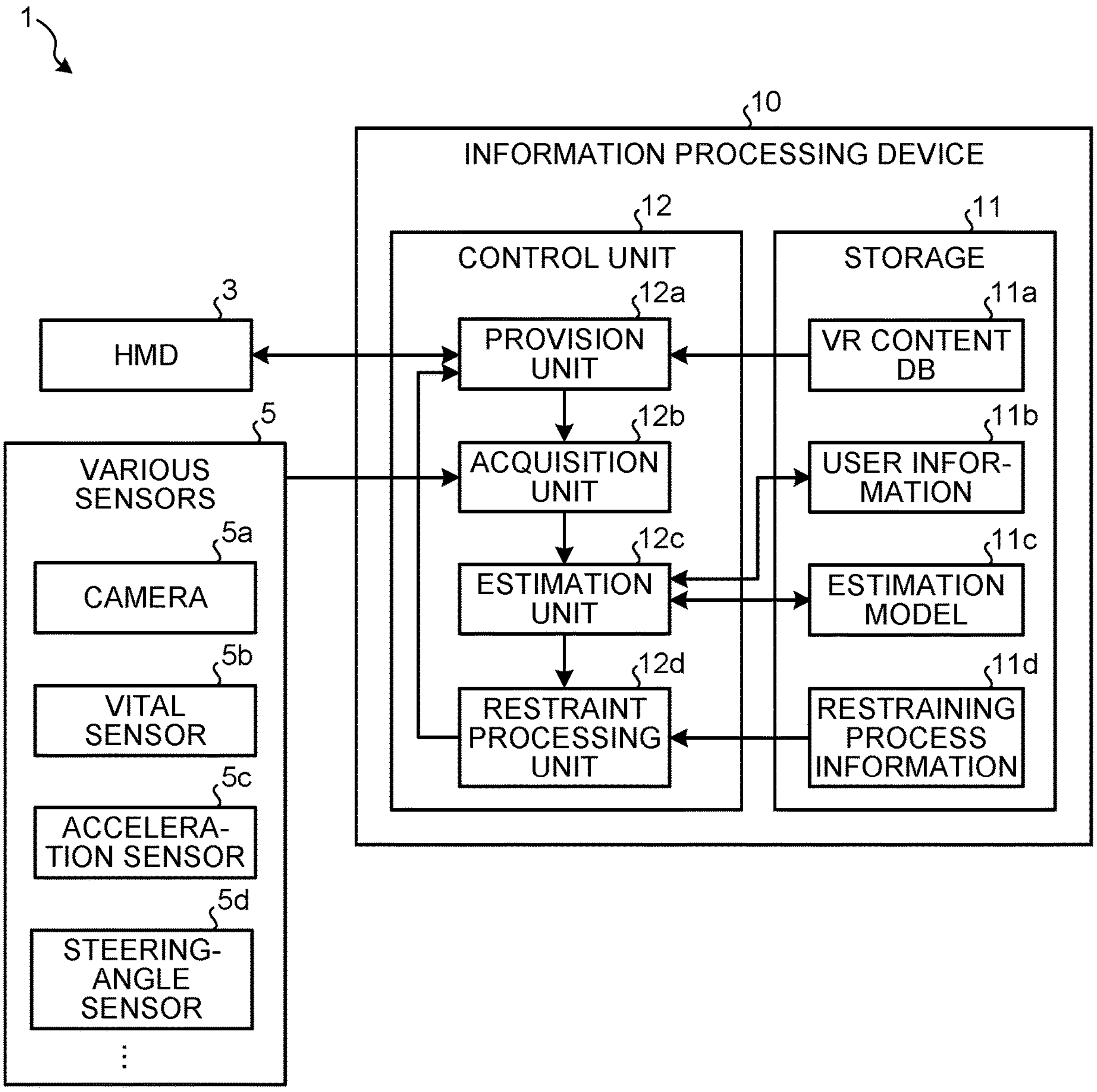
FIG. 4 is a block diagram illustrating a configuration example of an information processing system according to the first embodiment.

FIG. 4 is a block diagram illustrating a configuration example of the information processing system 1 according to the first embodiment. In FIG. 4 and the following FIGS. 9, 14, and 15, configuration elements alone are indicated, which are necessary for explaining features of the embodiments; and description of general configuration elements is omitted.

In other words, the configuration elements illustrated in FIGS. 4, 9, 14, and 15 are functionally conceptual, and thus they are not to be physically configured as illustrated in the drawings. Specific forms of distribution and integration of the configuration elements of the illustrated devices are not limited to those illustrated in the drawings, and all or some of the devices can be configured by separating or integrating the apparatus functionally or physically in any unit, according to various types of loads, the status of use, etc.

In the explanation with reference to FIGS. 4, 9, 14, and 15; details of the already-explained configuration element may be simplified or omitted.

As illustrated in FIG. 4, the information processing system 1 according to the first embodiment includes the HMD 3 and the information processing device 10.

The HMD 3 has been already explained with reference to FIG. 1, and explanation thereof is omitted here. The information processing device 10 includes a storage 11 and a control unit 12. The information processing device 10 is connected to various sensors 5.

The various sensors 5 include a sensor group configured to sense a state inside and outside of a vehicle, and further includes, for example, a camera 5*a*, a vital sensor 5*b*, an acceleration sensor 5*c*, a steering-angle sensor 5*d*, and the like.

The camera 5*a* includes a front camera, a rear camera, a side camera, an interior camera which are provided in a vehicle, and the like so as to capture inside and outside of the vehicle. The interior camera is configured to capture a state of the user U, for example.

The vital sensor 5*b* is a sensor configured to detect a physical state of the user U, and further is attached to the user U, for example, so as to measure vital data such as a heart rate, brain waves, a blood oxygen level, diaphoresis of the user U.

The acceleration sensor 5*c* measures an acceleration applied to a vehicle and/or a vehicle speed. The steering-angle sensor 5*d* measures a steering angle of a vehicle. Needless to say, the various sensors 5 may include a sensor other than the sensors 5*a* to 5*d* illustrated in FIG. 4.

For example, the storage 11 is realized by a semiconductor memory element such as a Random Access Memory (RAM) and a Flash Memory; and in the example illustrated in FIG. 4, the storage 11 stores therein a VR content database (VR content DB) 11*a*, user information 11*b*, an estimation model 11*c*, and restraining process information 11*d*.

The VR content DB 11*a* is a database that stores therein a VR content group to be provided to the HMD 3. The user information 11*b* is information related to a user using the HMD 3 so as to include, for example, the above-mentioned various parameters indicating a sickness tendency for each user and the like. The user information 11*b* is appropriately updated on the basis of an estimation result of a past state of VR sickness of the user U.

The estimation model 11*c* is an estimation model that is generated by using the above-mentioned algorithm of machine learning. For example, the estimation model 11*c* receives data indicating various states inside and outside of the user U, which are acquired by an acquisition unit 12*b* to be mentioned later, so as to output a value (for example, level value indicating degree of VR sickness) indicating a state of VR sickness of the user U.

The restraining process information 11*d* is information obtained by defining a restraining process of VR sickness to be executed in accordance with a degree of VR sickness of the user U. A specific example of the restraining process information 11*d* will be mentioned later with reference to FIG. 6.

The control unit 12 is a controller, for example, and a Central Processing Unit (CPU), a Micro Processing Unit (MPU), or the like executes not-illustrated various programs stored in the storage 11 by using a RAM as a work region so as to realize the control unit 12. The control unit 12 may be realized by an integrated circuit such as an Application Specific Integrated Circuit (ASIC) and a Field Programmable Gate Array (FPGA).

The control unit 12 includes a provision unit 12*a*, the acquisition unit 12*b*, an estimation unit 12*c*, and a restraint processing unit 12*d* so as to realize or execute function and working of information processing to be explained later.

The provision unit 12*a* provides a VR content stored in the VR content DB 11*a* to the HMD 3. The provision unit 12*a* acquires, at any time, change in a state detected by the sensor unit 33 of the HMD 3, and further reflects the above-mentioned change in the state on a VR content.

The acquisition unit 12*b* acquires, at any time, sensing data transmitted from the various sensors 5. The acquisition unit 12*b* acquires, at any time from the provision unit 12*a*, a use state of a VR content such as a type, a state of images, and a state of sounds of a VR content that are being provided. The acquisition unit 12*b* outputs the acquired various data to the estimation unit 12*c*.

The estimation unit 12*c* estimates a state of VR sickness of the user U by using the estimation model 11*c* on the basis of various data acquired by the acquisition unit 12*b*. The estimation unit 12*c* outputs the estimated estimation result to the restraint processing unit 12*d*.

The restraint processing unit 12*d* executes a restraining process of VR sickness related to sounds of a VR content in accordance with an estimation result of the estimation unit 12*c*.

Herein, details of the restraining process to be executed by the restraint processing unit 12*d* will be specifically explained with reference to FIG. 5 and FIG. 6. FIG. 5 is a diagram illustrating processing details of the restraining process according to the first embodiment. FIG. 6 is a diagram illustrating one example of the restraining process information 11*d* according to the first embodiment.

As illustrated in FIG. 5, a restraining process of VR sickness related to sounds of a VR content is "reducing process of sound image localization feeling", for example. In the reducing process of sound image localization feeling, the restraint processing unit 12*d* mixes a non-localized sound (monaural sound), for example. In a case where mixing the above-mentioned non-localized sound, the restraint processing unit 12*d* adjusts a mix ratio between a localized sound and a non-localized sound in accordance with a state of VR sickness.

For example, the restraint processing unit 12*d* more increases a mix ratio of a non-localized sound as a degree of VR sickness is larger. It is effective to gradually change a mix ratio between a localized sound and a non-localized sound. The restraint processing unit 12*d* may mix random noise as a non-localized sound.

In the reducing process of sound image localization feeling, the restraint processing unit 12*d* mixes a sound whose localization has no correlation with an image, for example. The above-mentioned sound is a healing sound and/or an environmental sound (sound of wind, sound of fire, etc.), for example. In a case where mixing the above-mentioned non-correlating sounds, the restraint processing unit 12*d* adjusts a mix ratio between a localized sound and a non-correlating sound in accordance with a state of VR sickness.

For example, the restraint processing unit 12*d* more increases a mix ratio of a non-correlating sound as a degree of VR sickness is larger.

In the reducing process of sound image localization feeling, the restraint processing unit 12*d* executes a sound localizing process, for example, but further limits a moving process thereof. In this case, the restraint processing unit 12*d* allows an instantaneous movement between two points, for example; however, does not allow a gradual movement. Specifically, for example, in a case where there present sound localized points A1, A2, A3, A4, and A5; a localized point is sequentially moved in a general sound localizing process, for example, in the order of A1→A2→A3→A4→A5. In this case, a timing to be moved to each of the localized points are decided for a corresponding localized point. In the reducing process of sound image localization feeling, the restraint processing unit 12*d* executes a sound localizing process for directly moving a localized point in the order of A1→A5, for example. The restraint processing unit 12*d* sets a timing of movement of A1→A5 to a timing of A3, for example.

In the reducing process of sound image localization feeling, the restraint processing unit 12*d* shorten a localization movement distance, for example. In this case, the restraint processing unit 12*d* does not change a localization movement time interval, for example. Specifically, for example, regarding the above-mentioned localized points A1, A2, A3, A4, and A5, the point is sequentially moved in the order of A1→A2→A3→A4→A5 in general; however, in the reducing process of sound image localization feeling, the restraint processing unit 12*d* executes a sound localizing process for moving the point in the order of A1→A2→A3, for example. In other words, a localization movement distance is shortened. In this case, the restraint processing unit 12*d* reduces a moving speed between A1→A2 or A2→A3 so as to move the point up to A3 over a time interval that is generally taken for the point to reach A5, for example. In other words, a localization movement time interval is not changed from normal one. Furthermore, the above-mentioned instantaneous movements may be combined so as to directly move the point in the order of A1→A3 without changing a localization movement time interval.

In the reducing process of sound image localization feeling, the restraint processing unit 12*d* outputs left and right sounds in antiphase, for example. Thus, a stereo effect becomes close to that of monaural sounds, for example.

In the reducing process of sound image localization feeling, the restraint processing unit 12*d* emphasizes and synthesizes a deep bass sound (having low directivity and provides little localization feeling), for example. In the reducing process of sound image localization feeling, the restraint processing unit 12*d* outputs a healing sound and/or an environmental sound (sound of wind, sound of fire, etc.), for example. This is a method for mixing another sound without processing a sound itself of a VR content so as to relatively make it hard to feel localization feeling by the sound of the VR content.

In the reducing process of sound image localization feeling, the restraint processing unit 12*d* synthesizes a sound of BGM (namely, constant mixed sound) at a large ratio, for example. In a case where synthesizing the above-mentioned sound of BGM at a large ratio, the restraint processing unit 12*d* adjusts a synthesis ratio in accordance with a state of VR sickness. This is also a method for mixing another sound so as to relatively make it hard to feel localization feeling by a sound of a VR content.

In the reducing process of sound image localization feeling, the restraint processing unit 12*d* switches a sound sensing source, for example. In this case, the restraint processing unit 12*d* switches a sound sensing source from the speaker 32 of the HMD 3 into, for example, a not-illustrated bone-conduction speaker, a not-illustrated body-sonic audio, or the like.

The restraint processing unit 12*d* may appropriately combine the above-mentioned reducing processes of sound image localization feeling.

As illustrated in FIG. 5, a restraining process of VR sickness related to sounds of a VR content is "reducing process of sound-volume changing speed", for example. As illustrated in FIG. 5, a restraining process of VR sickness related to sounds of a VR content is "restricting process of volume changing width", for example.

There present methods for generating sound image localization feeling by providing localization feeling to a sound source itself and by processing a sound transmitted from a sound source, the former method executes level adjustment, time phase adjustment, and the like, and further executes various type of mixing and the like on each of multi-track sound signals so as to strengthen or weaken localization feeling. The latter method adjusts each parameter of sound processing to be capable of strengthening or weakening localization feeling. A sound source itself of a single VR content is preliminarily recorded while including a data configuration constituted of a plurality of sound-source patterns whose sound image localization feelings, localization movement distances, volume changing widths, and the like are different from each other; and further may switch between the above-mentioned sound-source patterns in accordance with a state of VR sickness so as to switch a restraint effect level of VR sickness.

As illustrated in FIG. 6, a restraining process of VR sickness to be executed by the restraint processing unit 12*d* in accordance with a degree of VR sickness is associated with the restraining process information 11*d*. As illustrated in FIG. 6, a content type may be further associated with the restraining process information 11*d*.

In the example illustrated in FIG. 6, a degree of sickness gradually increases from L1 up to L3. A content type indicates that sickness is more easily gotten from A up to C.

A type in which sickness is easily gotten is, for example, action-oriented, horror-oriented, or the like.

In the example illustrated in FIG. 6, processes a, b, and c that are restraining processes related to sounds indicate that an intensity of a restraining process gradually increases from the process a up to the process c. In a case of the above-mentioned example illustrated in FIG. 6, if a degree of sickness is L1, the restraint processing unit 12*d* executes the process a only in a case where a content type is C.

If a degree of sickness is L2, in a case where a content type is B, the restraint processing unit 12*d* executes the process a, and in a case where a content type is C, the restraint processing unit 12*d* executes the process b whose intensity is larger than that of the process a.

If a degree of sickness is L3, in a case where a content type is A, the restraint processing unit 12*d* executes the process a, in a case where a content type is B, the restraint processing unit 12*d* executes the process b, and in a case where a content type is C, the restraint processing unit 12*d* executes the process c whose intensity is larger than those of the processes a and b.

In FIG. 6, the example is indicated in which a restraining process of VR sickness related to images is also defined, and it indicates that the restraining process of VR sickness related to images can be used in conjunction with a restraining process of VR sickness related to sounds. Note that similar to the above-mentioned processes a, b, and c; among the processes l, m, n, and o, an intensity of the restraining process gradually increases from the process l up to the process o.

Returning to explanation of FIG. 4. The restraint processing unit 12*d* executes the restraining process having explained with reference to FIG. 5 and FIG. 6 on the basis of an estimation result of the estimation unit 12*c* and the restraining process information 11*d* so as to reflect the above-mentioned execution result on a VR content to be provided to the HMD 3 by the provision unit 12*a*.

Figure 7:
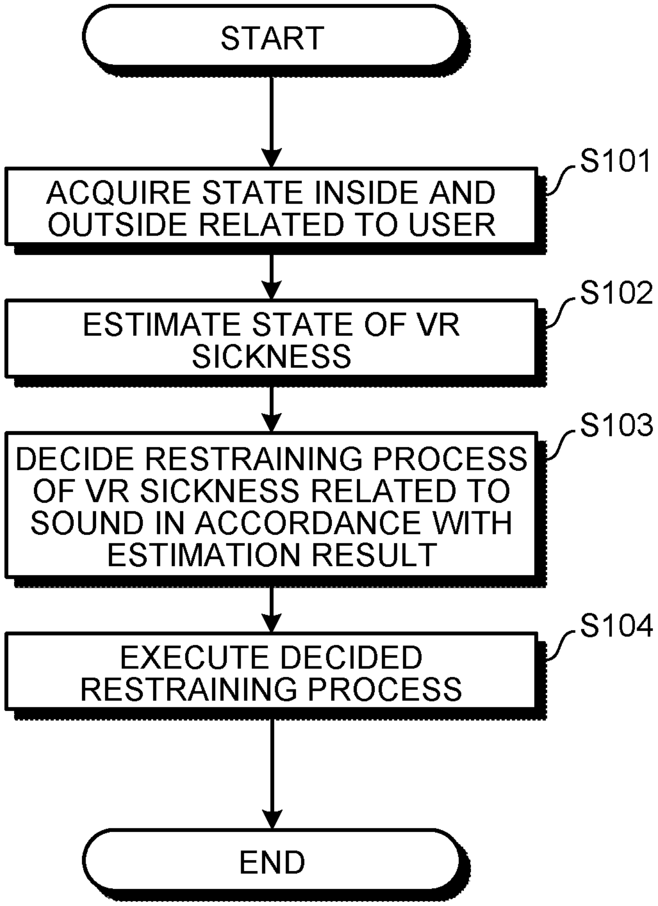
FIG. 7 is a flowchart illustrating a processing procedure to be executed by an information processing device according to the first embodiment.

Next, a processing procedure to be executed by the information processing device 10 according to the first embodiment will be explained with reference to FIG. 7. FIG. 7 is a flowchart illustrating a processing procedure to be executed by the information processing device 10 according to the first embodiment. The processing procedure illustrated in FIG. 7 is repeated at any time during a time interval in which the provision unit 12*a* is providing a VR content to the HMD 3.

As illustrated in FIG. 7, the acquisition unit 12*b* acquires a state inside and outside related to the user U (Step S101). The estimation unit 12*c* estimates a state of VR sickness of the user U on the basis of the acquired state (Step S102).

The restraint processing unit 12*d* decides a restraining process of VR sickness related to sounds in accordance with the estimated estimation result (Step S103). The restraint processing unit 12*d* executes the decided restraining process (Step S104), and further ends the processing.

As described above, the information processing device 10 according to the first embodiment includes the acquisition unit 12*b*, the estimation unit 12*c*, and the restraint processing unit 12*d*. The acquisition unit 12*b* acquires a state inside and outside related to the user U of a VR content (corresponding to one example of "digital content that includes virtual space experience"). The estimation unit 12*c* estimates a state of VR sickness (corresponding to one example "sickness") of the user U based on the state that is acquired by the acquisition unit 12*b*. The restraint processing unit 12*d* executes a restraining process of VR sickness related to sounds of the VR content in accordance with the state of VR sickness of the user U that is estimated by the estimation unit 12*c*.

Therefore, in accordance with the information processing device 10 according to the first embodiment, it is possible to restrict VR sickness of the user U due to a VR content. Particularly, it is possible to restrict VR sickness that is caused by synchronous deviation between sounds and images, and/or the fact that fluctuation in sounds and images is large and processing of a brain does not catch up with it.

The restraint processing unit 12*d* executes, as the restraining process, a reducing process of sound image localization feeling in the sound of the VR content.

Therefore, in accordance with the information processing device 10 according to the first embodiment, it is possible to restrict VR sickness of the user U due to a VR content by using a reducing process of sound image localization feeling without increasing a processing load.

The restraint processing unit 12*d* executes, as the restraining process, a reducing process of a sound-volume changing speed in the sound of the VR content.

Therefore, in accordance with the information processing device 10 according to the first embodiment, it is possible to restrict VR sickness of the user U due to a VR content by using a reducing process of a sound-volume changing speed without increasing a processing load.

The restraint processing unit 12*d* executes, as the restraining process, a restricting process of a volume changing width in the sound of the VR content.

Therefore, in accordance with the information processing device 10 according to the first embodiment, it is possible to restrict VR sickness of the user U due to a VR content by using a restricting process of a volume changing width without increasing a processing load.

Sound source data of the VR content includes a plurality of sound-source patterns at least whose sound image localization feelings, localization movement distances, or volume changing widths are different from each other, and the restraint processing unit 12*d* executes, as the restraining process, a switching process for switching between the sound-source patterns.

Therefore, in accordance with the information processing device 10 according to the first embodiment, a preliminarily-recorded sound-source pattern is switched, so that it is possible to switch a restraint effect level of VR sickness, for example.

2. Second Embodiment

Figure 8:
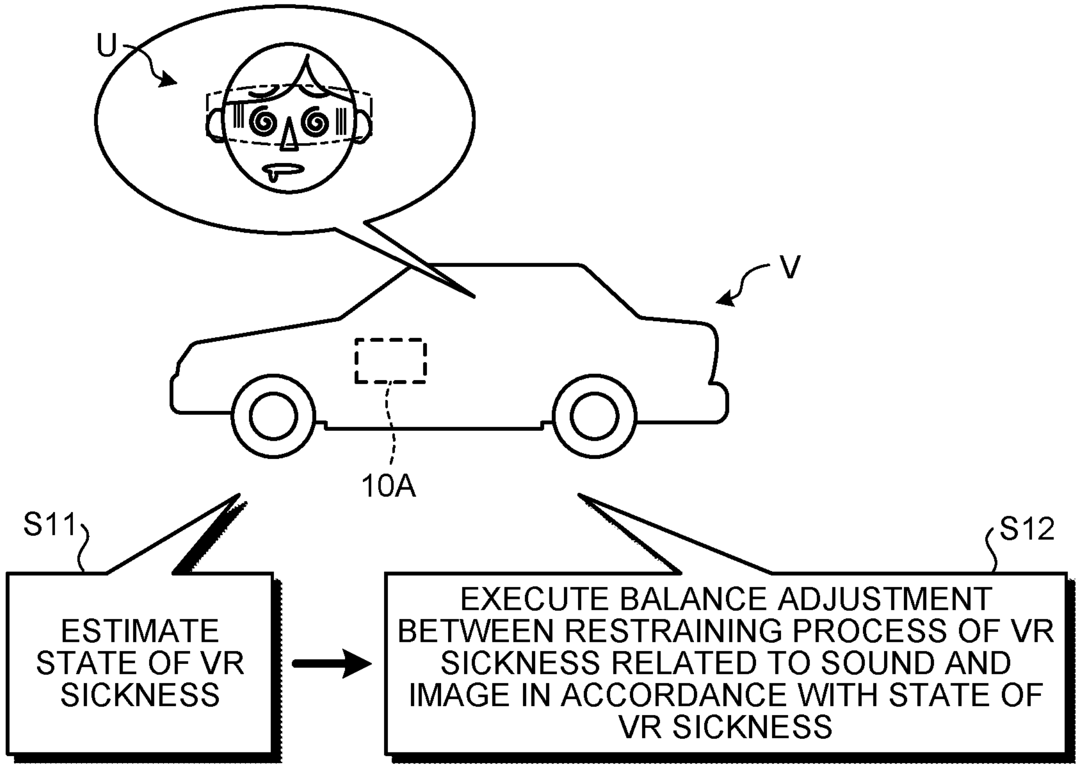
FIG. 8 is a diagram illustrating the outline of an information processing method according to a second embodiment.

Next, a second embodiment will be explained. In explanation of the second embodiment, explanation of a part duplicated with the first embodiment is simplified or omitted unless otherwise needed. The outline of an information processing method according to the second embodiment will be explained with reference to FIG. 8. FIG. 8 is a diagram illustrating the outline of an information processing method according to the second embodiment.

As already explained with reference to FIG. 2, VR sickness is caused by synchronous deviation between sounds and images, and/or the fact that fluctuation in sounds and images is large and processing of a brain does not catch up with it. Moreover, VR sickness can be caused by a gap between a sense by a VR experience that is enjoyed by using the HMD 3 and a perceptive sense of the user U him/herself caused by change in a peripheral environment.

Therefore, an information processing method according to the second embodiment includes: acquiring a state inside and outside related to the user U; estimating a state of VR sickness of the user U on the basis of the acquired state; and executing a restraining process of VR sickness related to sounds and images in accordance with the estimated state of VR sickness. In this case, balance adjustment between a restraining process related to sounds and a restraining process related to images is executed in accordance with a state of VR sickness.

Specifically, as illustrated in FIG. 8, in an information processing method according to the second embodiment, an information processing device 10A according to the second embodiment acquires, at any time, a state inside and outside related to the user U, and further estimates a state of VR sickness of the user U (Step S11). For example, the information processing device 10A detects change in a physical state of the user U so as to estimate a state of VR sickness.

For example, the information processing device 10A estimates a state of VR sickness on the basis of a use state of a VR content such as a type, state of images, and a state of sounds of a VR content during provision.

For example, the information processing device 10A estimates a state of VR sickness on the basis of a traveling state of a vehicle such as a road state, a state of a vehicle, and an operation state. For example, the information processing device 10A estimates a state of VR sickness on the basis of user information that includes various parameters indicating a sickness tendency for each user, etc.

In the above-mentioned estimating process of the state of VR sickness, for example, the information processing device 10A may use an estimation model that is generated by using algorithm of machine learning. Reinforcement learning is appropriately executed on the above-mentioned estimation model on the basis of an estimation result of an actual state of VR sickness. For example, as a result of the reinforcement learning, a determination threshold for estimating a state of VR sickness and the like are appropriately updated.

The information processing device 10A executes a restraining process of VR sickness related to each of sounds and images of a VR content, in accordance with an estimation result in Step S11. In outline, a restraining process of VR sickness related to sounds is for reducing stimulation related to sounds of a VR content, and is a reducing process of sound image localization feeling, for example. In outline, a restraining process of VR sickness related to images is for reducing stimulation related to images of a VR content, and is a reducing process of, for example, contrast, a color tone, and the like.

As described above, stimulation related to sounds and images of a VR content is weakened, so that it is possible to reduce a sickness tendency that is evoked by sounds and images of a VR content. In other words, it is possible to contribute to restriction on VR sickness of the user U due to a VR content.

Additionally, in an information processing method according to the second embodiment, when executing a restraining process of VR sickness related to each of sounds and images of a VR content, the information processing device 10A executes balance adjustment between a restraining process of VR sickness related to sounds and images in accordance with a state of VR sickness of the user U (Step S12).

Thus, it is possible to restrict VR sickness of the user U due to a VR content while maintaining effects of VR experience by a VR content as much as possible.

As described above, the information processing method according to the second embodiment includes: acquiring a state inside and outside related to the user U; estimating a state of VR sickness of the user U on the basis of the acquired state; and executing a restraining process of VR sickness related to sounds and images in accordance with the estimated state of VR sickness. In this case, the information processing method according to the second embodiment includes executing balance adjustment between a restraining process related to images and a restraining process related to sounds in accordance with a state of VR sickness.

Therefore, in accordance with the information processing method according to the second embodiment, it is possible to restrict VR sickness of the user U due to a VR content. Hereinafter, a configuration example of the information processing system 1A will be more specifically explained, to which the information processing method according to the second embodiment is applied.

Figure 9:
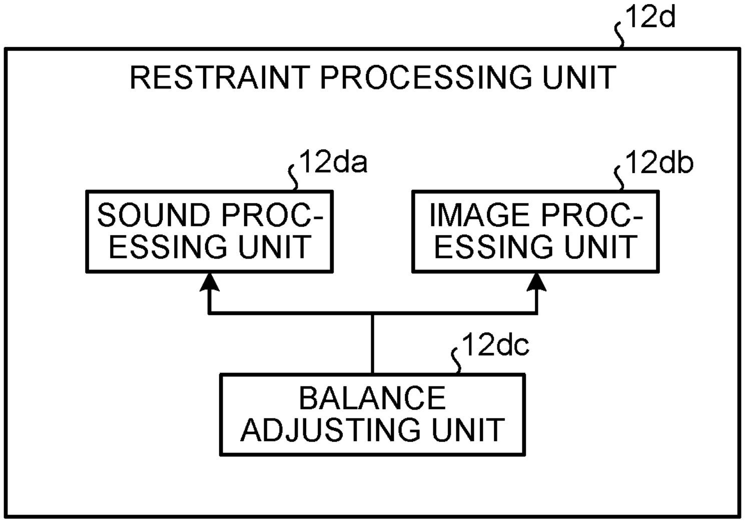
FIG. 9 is a block diagram illustrating a configuration example of a restraint processing unit according to the second embodiment.

FIG. 9 is a block diagram illustrating a configuration example of the restraint processing unit 12*d* according to the second embodiment. An overall configuration example of the information processing system 1A according to the second embodiment is similar to that of the information processing system 1 illustrated in FIG. 4, and thus explanation thereof is omitted here.

The restraint processing unit 12*d* according to the second embodiment executes a restraining process of VR sickness related to sounds and images of a VR content in accordance with an estimation result of the estimation unit 12*c* while executing balance adjustment between restraint of VR sickness using sounds and restraint of VR sickness using images.

As illustrated in FIG. 9, the restraint processing unit 12*d* includes a sound processing unit 12*da*, an image processing unit 12*db*, and a balance adjusting unit 12*dc*. The sound processing unit 12*da* executes a restraining process of VR sickness related to sounds of a VR content. The image processing unit 12*db* executes a restraining process of VR sickness related to images of a VR content.

The balance adjusting unit 12*dc* executes balance adjustment between sound processing using the sound processing unit 12*da* and image processing using the image processing unit 12*db* in accordance with an estimation result of the estimation unit 12*c*.

Details of the restraining process to be executed by the restraint processing unit 12*d* according to the second embodiment will be more specifically explained with reference to FIG. 10 and FIG. 11. FIG. 10 is a diagram illustrating processing details of a restraining process according to the second embodiment. FIG. 11 is a diagram illustrating one example of the restraining process information 11*d* according to the second embodiment.

As illustrated in FIG. 10, the balance adjusting unit 12*dc* of the restraint processing unit 12*d* executes "balance adjustment according to degree of VR sickness" of the user U, which is estimated by the estimation unit 12*c*, for example. Specifically, as illustrated in FIG. 10, for example, in a case where the user U has a light VR sickness, the balance adjusting unit 12*dc* mainly executes a restraining process related to sounds. The above-mentioned "mainly executing restraining process related to sounds" includes execution of a restraining process related to sounds alone.

For example, generally, an information amount of sounds is smaller than that of images, and thus effects for restraining VR sickness is considered to be smaller in execution of a restraining process related to sounds than in a restraining process related to images. In other words, in a case where a restraining process related to images is executed, effects for restraining VR sickness are large; however, effects of VR experience may decrease.

Thus, in a case where the user U has a light VR sickness, a restraining process related to sounds is mainly executed to be capable of restricting VR sickness of the user U while maintaining effects of VR experience by a VR content as much as possible.

As illustrated in FIG. 10, for example, in a case where the user U has a middle VR sickness, the balance adjusting unit 12*dc* mainly executes a restraining process related to images. The above-mentioned "mainly executing restraining process related to images" includes a case where a restraining process related to images alone is executed.

Thus, even in a case where the user U has a middle VR sickness, it is possible to restrict VR sickness of the user U while maintaining effects of VR experience by a VR content as much as possible.

As illustrated in FIG. 10, the balance adjusting unit 12*dc* may execute a restraining process related to each of sounds and images at a corresponding intensity that is decided in accordance with an extent of VR sickness of the user U. This point will be mentioned later with reference to FIG. 11.

As illustrated in FIG. 10, the balance adjusting unit 12*dc* is capable of executing "balance adjustment related to sounds" on a plurality of sounds. In this case, the balance adjusting unit 12*dc* causes the sound processing unit 12*da* not to simply add sounds to each other, but to synthesize sounds with each other in accordance with environment.

Specifically, for example, in a case where outputting a sound of a virtual object corresponding to each of two vehicles located outside of a vehicle in a VR content, the balance adjusting unit 12*dc* synthesizes sounds such that a part of a sound from a farther vehicle viewed from a listening position (namely, position of user U) is shut by a closer vehicle, similarly to a case of the reality space.

Thus, it is possible to reduce a gap between a sense in a virtual space and a sense in a reality space, and further to restrict VR sickness of the user U while maintaining effects of VR experience by a VR content as much as possible.

Note that the restraining process related to sounds includes, for example, a reducing process of sound image localization feeling, a reducing process of a sound-volume changing speed, a restricting process of a volume changing width, and the like.

In the reducing process of sound image localization feeling, the sound processing unit 12*da* mixes a non-localized sound (monaural sound), for example. In a case where mixing the above-mentioned non-localized sound, the sound processing unit 12*da* adjusts a mix ratio between a localized sound and a non-localized sound in accordance with a state of VR sickness.

For example, the sound processing unit 12*da* more increases a mix ratio of a non-localized sound as a degree of VR sickness is larger. It is effective to gradually change a mix ratio between a localized sound and a non-localized sound. The sound processing unit 12*da* may mix random noise as a non-localized sound.

In the reducing process of sound image localization feeling, the sound processing unit 12*da* mixes a sound whose localization has no correlation with an image, for example. The above-mentioned sound is a healing sound and/or an environmental sound (sound of wind, sound of fire, etc.), for example. In a case where mixing the above-mentioned non-correlating sounds, the sound processing unit 12*da* adjusts a mix ratio between a localized sound and a non-correlating sound in accordance with a state of VR sickness.

For example, the sound processing unit 12*da* more increases a mix ratio of a non-correlating sound as a degree of VR sickness is larger.

In the reducing process of sound image localization feeling, the sound processing unit 12*da* executes a sound localizing process, for example; however, does not allow a moving process thereof. In this case, the sound processing unit 12*da* allows an instantaneous movement between two points; however, does not allow a gradual movement.

In the reducing process of sound image localization feeling, the sound processing unit 12*da* shortens a localization movement distance, for example. In this case, the sound processing unit 12*da* does not change a localization movement time interval.

In the reducing process of sound image localization feeling, the sound processing unit 12*da* outputs left and right sounds in antiphase, for example. Thus, a stereo effect is close to that of monaural sounds, for example.

In the reducing process of sound image localization feeling, the sound processing unit 12*da* emphasizes and synthesizes a deep bass sound, for example. In the reducing process of sound image localization feeling, the sound processing unit 12*da* outputs a healing sound and/or an environmental sound (sound of wind, sound of fire, etc.), for example. This is a method for not processing a sound itself of a VR content.

In the reducing process of sound image localization feeling, the sound processing unit 12*da* synthesizes a sound of BGM (namely, constant mixed sound) at a large ratio, for example. In a case where synthesizing the above-mentioned sound of BGM at a large ratio, the sound processing unit 12*da* adjusts a synthesis ratio in accordance with a state of VR sickness.

In the reducing process of sound image localization feeling, the sound processing unit 12*da* switches a sound sensing source, for example. In this case, the sound processing unit 12*da* switches a sound sensing source from the speaker 32 of the HMD 3 into, for example, a not-illustrated bone-conduction speaker, a not-illustrated body-sonic audio, or the like.

The sound processing unit 12*da* may appropriately combine the above-mentioned reducing processes of sound image localization feeling.

There present methods for generating sound image localization feeling by providing localization feeling to a sound source itself and by processing a sound transmitted from a sound source, the former method executes level adjustment, time phase adjustment, and the like, and further executes various type of mixing and the like on each of multi-track sound signals so as to strengthen or weaken localization feeling. The latter method adjusts each parameter of sound processing to be capable of strengthening or weakening localization feeling. A sound source itself of a single VR content is preliminarily recorded while including a data configuration constituted of a plurality of sound-source patterns whose sound image localization feelings, localization movement distances, volume changing widths, and the like are different from each other; and further may switch between the above-mentioned sound-source patterns in accordance with a state of VR sickness so as to switch a restraint effect level of VR sickness.

For example, the restraining process related to images includes a reducing process of contrast, luminance, a luminance changing width, and the like, an adjusting process of perspective feeling (apparent change amount of distant image is small and hardly provides sickness), a reducing process of a moving speed of a virtual object, and the like.

For example, the reducing process of contrast, luminance, a luminance changing width, and the like is realized by an image process executed by the image processing unit 12*db*; however, may be realized by display driving control. In the perspective feeling adjusting process, image data itself of a single VR content may be preliminarily recorded while including therein a data configuration that is constituted of a plurality of image patterns having different perspective feelings, and the image processing unit 12*db* may switch between these image patterns in accordance with a state of VR sickness so as to switch a restraint effect level of VR sickness. In this case, the above-mentioned switching process between sound-source patterns may be executed while keeping balance with respect to an image pattern.

As illustrated in FIG. 11, the restraining process information 11*d* according to the second embodiment is associated with a restraining process of VR sickness related to each of sounds and images to be executed by the restraint processing unit 12*d* in accordance with a degree of VR sickness. As illustrated in FIG. 6, a content type may be further associated with the restraining process information 11*d*.

In the example illustrated in FIG. 11, a degree of sickness gradually increases from L1 up to L3. A content type indicates that sickness is more easily gotten from A up to C. A type in which sickness is easily gotten is, for example, action-oriented, horror-oriented, or the like.

In the example illustrated in FIG. 11, processes a, b, and c that are restraining processes related to sounds indicate that an intensity of a restraining process gradually increases from the process a up to the process c. Numeric values of 1, 2, and 3, which are respectively provided to the processes a, b, and c, indicate that an intensity of a restraining process gradually increases from 1 up to 3. For example, with respect to the process a, a relation between intensities is $a1<a2<a3$.

The same is applied to processes 1, m, and n that are restraining processes related to images. For example, with respect to the process m, a relation between intensities is $m1<m2<m3$.

On the basis of the above-mentioned, in the example illustrated in FIG. 11, in a case where a degree of sickness is L1 and a content type is A, the restraint processing unit 12*d* executes a process a1 related to sounds alone. In a case where a content type is B, the restraint processing unit 12*d* individually executes, on sounds, a process a2 whose intensity is larger than that of the process a1; and further executes a process 12 on images. In a case where a content type is C, the restraint processing unit 12*d* individually executes, on sounds, a process a3 whose intensity is larger than that of the process a2; and further executes, on images, a process 13 whose intensity is larger than that of the process 12.

In a case where a degree of sickness is L2 and a content type is A, the restraint processing unit 12*d* individually executes, on sounds, a process b1 whose intensity is larger than those of the processes a1 to a3; and further executes, on images, a process m1 whose intensity is larger than those of the processes 12 and 13. In a case where a content type is B, the restraint processing unit 12*d* individually executes, on sounds, a process b2 whose intensity is larger than that of the process b1; and further executes, on images, a process m2 whose intensity is larger than that of the process m1. In a case where a content type is C, the restraint processing unit 12*d* individually executes, on sounds, a process b3 whose intensity is larger than that of the process b2; and further executes, on images, a process m3 whose intensity is larger than that of the process m2.

Similarly, in a case where a degree of sickness is L3 and a content type is A, the restraint processing unit 12*d* individually executes, on sounds, a process c1 whose intensity is larger than those of the processes b1 to b3; and further executes, on images, a process n1 whose intensity is larger than those of the processes m1 to m3. In a case where a content type is B, the restraint processing unit 12*d* individually executes, on sounds, a process c2 whose intensity is larger than that of the process c1; and further executes, on images, a process n2 whose intensity is larger than that of the process n1. In a case where a content type is C, the restraint processing unit 12*d* individually executes, on sounds, a process c3 whose intensity is larger than that of the process c2; and further executes, on images, a process n3 whose intensity is larger than that of the process n2.

Returning to explanation of FIG. 9. The restraint processing unit 12*d* executes the restraining process having explained with reference to FIG. 10 and FIG. 11 on the basis of an estimation result of the estimation unit 12*c* and the restraining process information 11*d* so as to reflect the above-mentioned execution result on a VR content to be provided to the HMD 3 by the provision unit 12*a*.

Figure 12:
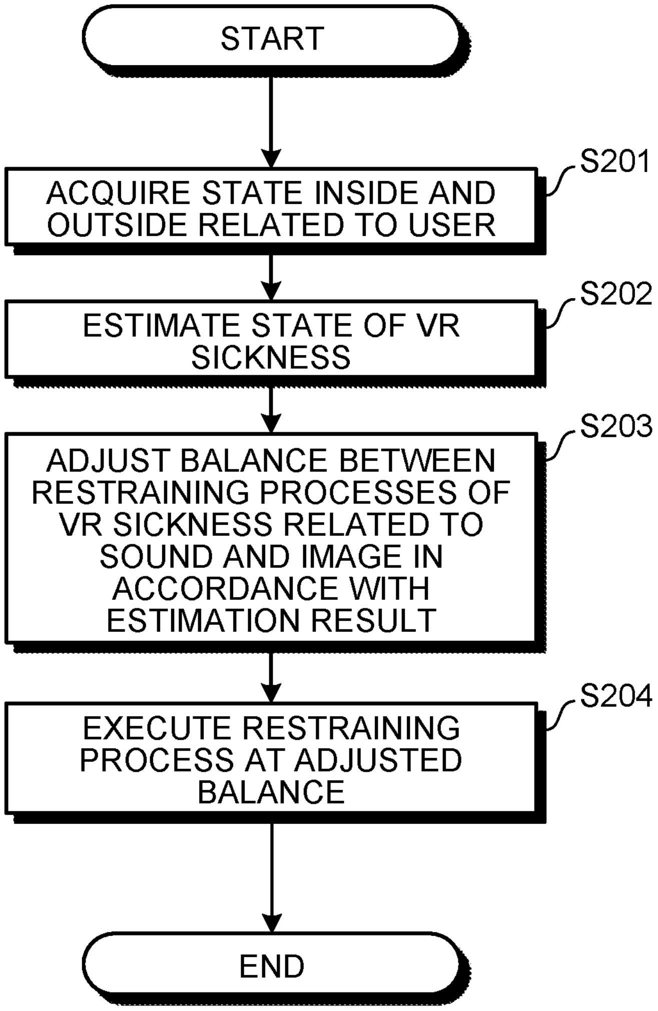
FIG. 12 is a flowchart illustrating a processing procedure to be executed by an information processing device according to the second embodiment.

Next, a processing procedure to be executed by the information processing device 10A according to the second embodiment will be explained with reference to FIG. 12. FIG. 12 is a flowchart illustrating a processing procedure to be executed by the information processing device 10A according to the second embodiment. The processing procedure illustrated in FIG. 12 is repeated at any time during a time interval in which the provision unit 12*a* is providing a VR content to the HMD 3.

As illustrated in FIG. 12, the acquisition unit 12*b* acquires a state inside and outside related to the user U (Step S201). The estimation unit 12*c* estimates a state of VR sickness of the user U on the basis of the acquired state (Step S202).

The restraint processing unit 12*d* adjusts balance between restraining processes of VR sickness related to sounds and images in accordance with the estimated estimation result (Step S203). The restraint processing unit 12*d* executes the restraining process at the adjusted balance (Step S204), and further ends the processing.

As described above, the information processing device 10A according to the second embodiment includes the acquisition unit 12*b*, the estimation unit 12*c*, and the restraint processing unit 12*d*. The acquisition unit 12*b* acquires a state inside and outside related to the user U of a VR content (corresponding to one example of "digital content that includes virtual space experience"). The estimation unit 12*c* estimates a state of VR sickness (corresponding to one example of "sickness") of the user U based on the state that is acquired by the acquisition unit 12*b*. The restraint processing unit 12*d* executes a restraining process of VR sickness related to the sound and the image of the VR content in accordance with the state of VR sickness of the user U that is estimated by the estimation unit 12*c*. When executing the restraining process, the restraint processing unit 12*d* executes balance adjustment between the restraining process related to the sound and the restraining process related to the image in accordance with the state of VR sickness of the user U.

Therefore, in accordance with the information processing device 10A according to the second embodiment, it is possible to restrict VR sickness of the user U due to a VR content. Particularly, it is possible to restrict VR sickness that is caused by synchronous deviation between sounds and images, and/or the fact that fluctuation in sounds and images is large and processing of a brain does not catch up with it.

Moreover, it is possible to restrict VR sickness of the user U due to a VR content while maintaining effects of VR experience by the VR content as much as possible.

In a case where a degree indicating the state of VR sickness is a light degree, the restraint processing unit 12*d* mainly executes the restraining process related to the sound.

Therefore, in accordance with the information processing device 10A according to the second embodiment, it is possible to restrict VR sickness of the user U due to a VR content while maintaining effects of VR experience by the VR content as much as possible.

In a case where a degree indicating the state of VR sickness is a light degree, the restraint processing unit 12*d* executes the restraining process related to the sound alone.

Therefore, in accordance with the information processing device 10A according to the second embodiment, it is possible to restrict VR sickness of the user U due to a VR content without increasing a processing load while maintaining effects of VR experience by the VR content as much as possible.

In a case where a degree indicating the state of VR sickness is a middle extent, the restraint processing unit 12*d* mainly executes the restraining process related to the image.

Therefore, in accordance with the information processing device 10A according to the second embodiment, in a case where VR sickness of the user U is equal to or more than a light degree, it is possible to quickly reduce VR sickness of the user U due to a VR content.

The restraint processing unit 12*d* executes the restraining process related to each of the sound and the image at a corresponding intensity that is decided in accordance with a degree indicating the state of VR sickness.

Therefore, in accordance with the information processing device 10A according to the second embodiment, it is possible to execute a restraining process related to each of sounds and images at an appropriate balance according to VR sickness of the user U.

Image data of the VR content includes a plurality of image patterns at least whose perspective feelings are different from each other, and the restraint processing unit 12*d* executes, as the restraining process related to the image, a switching process for switching between the image patterns.

Therefore, in accordance with the information processing device 10A according to the second embodiment, preliminarily-recorded image patterns are switched therebetween to be able to switch a restraint effect level of VR sickness, for example.

Sound source data of the VR content includes a plurality of sound-source patterns at least whose sound image localization feelings, localization movement distances, or volume changing widths are different from each other, and the restraint processing unit 12*d* executes, as the restraining process related to the sound, a switching process for switching between the sound-source patterns while keeping balance with respect to the image pattern.

Therefore, in accordance with the information processing device 10A according to the second embodiment, a preliminarily-recorded sound-source pattern is switched while taking balance with respect to an image pattern, so that it is possible to execute switching of a restraint effect level of VR sickness, which is appropriately balanced in terms of a visual sense and an auditory sense.

3. Third Embodiment

Figure 13:
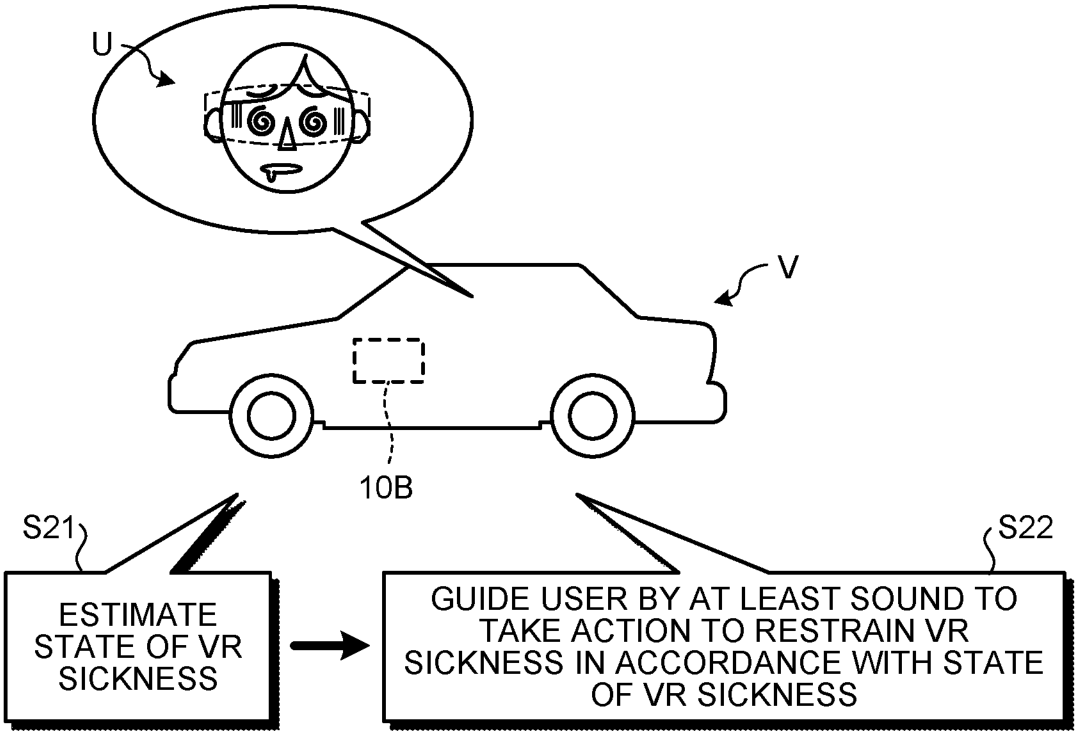
FIG. 13 is a diagram illustrating the outline of an information processing method according to a third embodiment.

Next, a third embodiment will be explained. In explanation of the third embodiment, explanation of a part duplicated with the first embodiment and the second embodiment is simplified or omitted unless otherwise needed. The outline of an information processing method according to the third embodiment will be explained with reference to FIG. 13. FIG. 13 is a diagram illustrating the outline of an information processing method according to the third embodiment.

As described hereinbefore, the VR sickness can be caused by synchronous deviation between sounds and images, and/or the fact that fluctuation in sounds and images is large and processing of a brain does not catch up with it. Furthermore, VR sickness can be caused by a deviation between a sense in VR experience enjoyed by using HMD 3 and a sense in a real body of the user U himself caused by peripheral environmental change.

Particularly, for on-vehicle systems like the information processing systems 1 and 1A as explained hereinbefore, the above-mentioned deviation of sense is easy to be caused by a sudden change of a behavior of the vehicle under the state that the user U is not prepared physically or mentally.

Therefore, taking the state that the user U is not prepared physically or mentally into consideration, an information processing method according to the third embodiment is configured to include: acquiring a state inside and outside related to the user U, estimating a VR sickness state of the user U based on the acquired state, and guiding the user U at least by a sound in such a manner that the user U takes an action to restrict VR sickness in accordance with the estimated VR sickness state.

Specifically, as illustrated in FIG. 13, according to an information processing method in the third embodiment, an information processing device 10B acquires, at any time, a state of inside and outside related to the user U, and further estimates a VR sickness state of the user U (Step S21). For example, the information processing device 10B detects a change in a physical state of the user U so as to estimate the VR sickness state.

Furthermore, the information processing device 10B estimates the VR sickness state based on a using condition of a VR content such as a type or an image condition or a sound condition of a VR content during provision.

Furthermore, the information processing device 10B estimates the VR sickness state based on a vehicle traveling state such as a road state, a vehicle state, and a vehicle operation state. The information processing device 10B also estimates the VR sickness state based on user information including various kinds of parameters indicating such as sickness tendencies of respective users.

An estimation model generated by using such as algorithm for machine learning can be used as the information processing device 10B in the above-mentioned estimating process of the VR sickness state. Such the estimation model is appropriately reinforced in learning based on an estimation result of an actual VR sickness state. As a result of the reinforcement learning, for example, a determination threshold for estimating the VR sickness state is appropriately updated.

Next, the information processing device 10B guides at least by a sound in such a manner that the user U takes an action to restrict the VR sickness, based on the estimation result in Step S21 (Step S22). For example, the information processing device 10B generates a guidance sound in such a manner that the user U takes an action to restrict the VR sickness.

As one example, the information processing device 10B generates a guidance sound in such a manner that the user U looks at a direction that makes difficult to perceive vibration or shaking. Such direction is, for example, a distant place.

Such distant place is a direction that, for example, a depth direction and an image fluctuation is small for a VR space in which the display 31 is a nontransparent-type and is isolated from a real space. Furthermore, for an MR space in which the display 31 is a transparent-type and is seamless with a real space, it is literally distant place in a real space or a direction in which an image fluctuation of a camera provided in a running vehicle is small.

Accordingly, the sickness tendency caused by a sound and an image of a VR content can be reduced by guiding the user U to take an action to restrict the VR sickness. In other words, it can contribute to restrict the VR sickness of the user U caused by a VR content.

It's to be noted that not only a sound but also an image or a vibration can be used when guiding the user U to take an action to restrict VR sickness. Specific examples will be explained later with reference to FIG. 16 and FIG. 17.

As described in the above, the information processing method of the third embodiment executes a restraining process of VR sickness, which includes: acquiring a state inside and outside related to the user U; estimating a state of VR sickness of the user U on the basis of the acquired state; and guiding the user U by at least a sound to take an action to restrict VR sickness in accordance with the estimated state of VR sickness.

Therefore, in accordance with the information processing method according to the third embodiment, it is possible to restrict VR sickness of the user U due to a VR content. Hereinafter, a configuration example of the information processing system 1B will be more specifically explained, to which the information processing method according to the third embodiment is applied.

Figure 14:
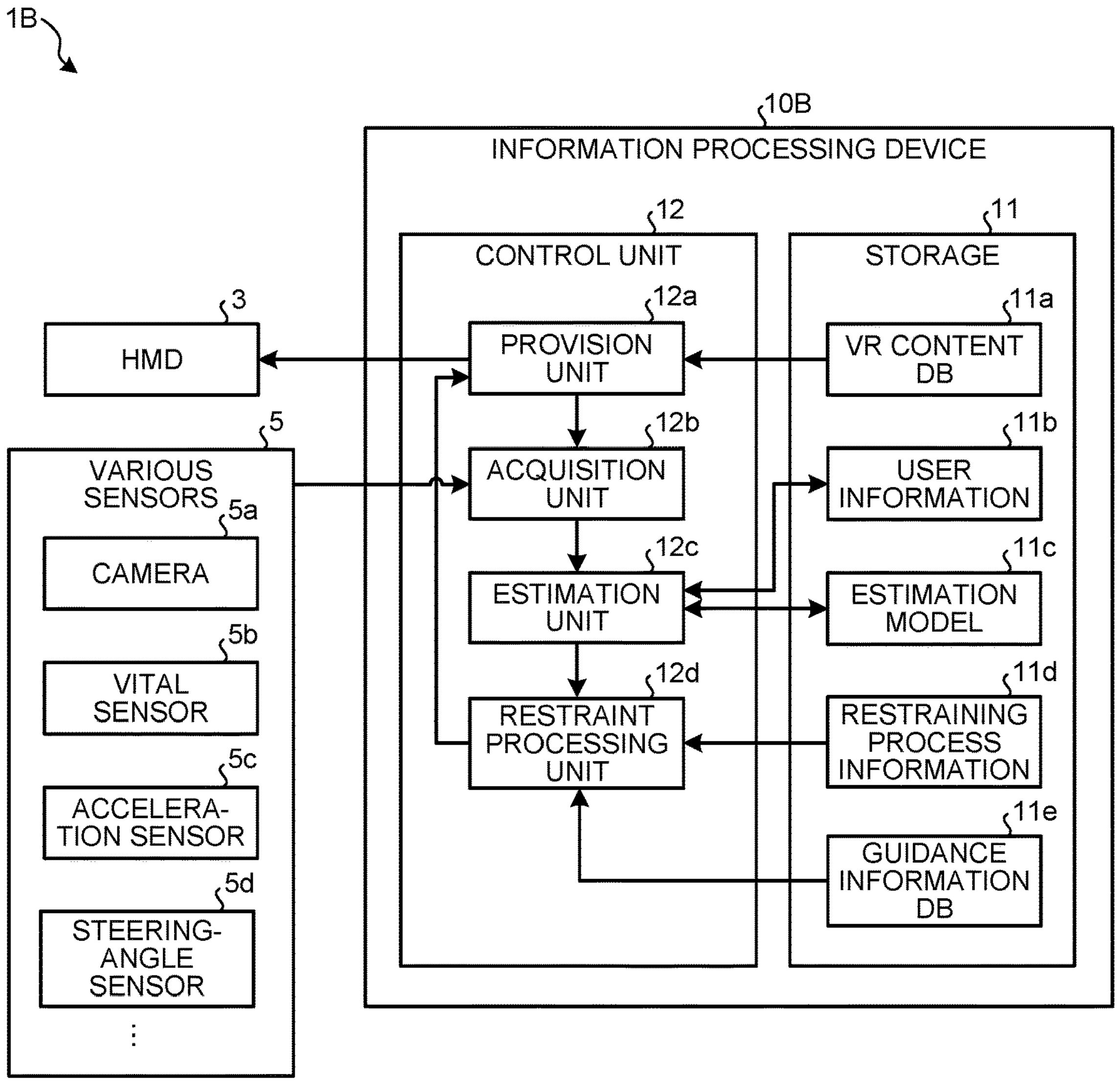
FIG. 14 is a block diagram illustrating a configuration example of an information processing system according to the third embodiment.
Figure 15:
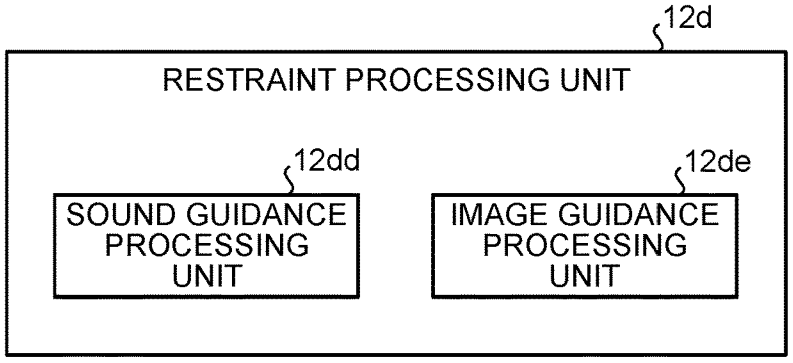
FIG. 15 is a block diagram illustrating a configuration example of a restraint processing unit according to the third embodiment.

FIG. 14 is a block diagram illustrating a configuration example of the information processing system 1B according to the third embodiment. FIG. 15 is a block diagram illustrating a configuration example of the restraint processing unit 12*d* according to the third embodiment. Since FIG. 14 and FIG. 15 correspond to FIG. 4 and FIG. 9, respectively, different points from FIG. 4 and FIG. 9 will be mainly explained.

As illustrated in FIG. 14, the information processing system 1B according to the third embodiment is different from that illustrated in FIG. 4 in that the storage 11 of the information processing device 10B further stores therein a guidance information DB 11*e*.

The guidance information DB 11*e* is a database of information related to such as a sound and an image for guiding the user U to take an action to restrict VR sickness, and stores, for example, such as sound source data of the guidance sound described above.

The restraint processing unit 12*d* according to the third embodiment executes a restraining process of VR sickness related to sounds and images of a VR content in accordance with an estimation result of the estimation unit 12*c*. As one example of the above-mentioned restraining process, the restraint processing unit 12*d* guides the user U at least by a sound in such a manner that the user U takes an action to restrict VR sickness in accordance with the estimation result of the estimation unit 12*c*.

As illustrated in FIG. 15, it is different from FIG. 9 that the restraint processing unit 12*d* has a sound guidance processing unit 12*dd* and an image guidance processing unit 12*de* instead of the sound processing unit 12*da*, the image processing unit 12*db*, and the balance adjusting unit 12*dc* described hereinbefore. The sound guidance processing unit 12*dd* executes a sound guidance process to guide the user U by using a sound in such a manner that the user U takes an action to restrict VR sickness. The image guidance processing unit 12*de* executes an image guidance process to guide the user U by using an image in such a manner that the user U takes an action to restrict VR sickness.

Details of the restraining process to be executed by the restraint processing unit 12*d* according to the third embodiment will be more specifically explained with reference to FIG. 16 and FIG. 17. FIG. 16 is a diagram illustrating processing details of a restraining process according to the third embodiment. FIG. 17 is a diagram illustrating one example of the restraining process information 11*d* according to the third embodiment.

As illustrated in FIG. 16, the restraint processing unit 12*d* executes the restraining process to guide, for example, a gaze of the user U. As described hereinbefore, the restraint processing unit 12*d* generates a guidance sound that urges the user U to move his/her gaze into a direction (for example, toward the above described "distant place") in which a vibration is hardly perceived, for example. In this case, it may be guided not only by a sound but also an image in addition to the sound. When it is guided by the image, the gaze of the user U may be guided, for example, by displaying a virtual object for guiding in a VR space, and moving the virtual object.

As illustrated in FIG. 16, the restraint processing unit 12*d* executes the restraining process that urges the user U to take a posture in which the user U hardly gets sickness. The restraint processing unit 12*d* generates a nasty sound such as buzzing of a mosquito or a bee in accordance with a vibration generated at, for example, a curve based on a traveling state acquired by the acquisition unit 12*b*, and guides a head portion of the user U to a position and a direction in which a vibration hardly occurs at semicircular canals according to movement of a sound image of the generated sound.

Specifically, the restraint processing unit 12*d* generates the sound of buzzing of a mosquito or a bee toward the left side of the head portion of the user U in a case of a left curve, and guides the user U to incline his/her head portion to the right side so as to avoid the sound in a reflex manner. The restraint processing unit 12*d* guides the user U to look up by generating an attention sound above the user U in a case of a rising slope and the like.

As illustrated in FIG. 16, the restraint processing unit 12*d* executes the restraining process to output an alarm sound for, for example, an estimated behavior of a vehicle. Specifically, the restraint processing unit 12*d* makes an announcement of a specific guidance of "there presents level difference ahead" in a case where, for example, there presents a level difference ahead.

As illustrated in FIG. 16, the restraint processing unit 12*d* executes the restraining process to guide the user U, for example, to utter. Specifically, the restraint processing unit 12*d* makes, for example, an appearance of an avatar in a VR space in accordance with a VR sickness state of the user U so as to encourage a conversation to the user U.

In a case where a VR content is a game, the restraint processing unit 12*d* may add thereto a mission, for example, forcing the user to sing a song, to join a quiz game or a word-chain game, and the like, which is necessary for the user to utter as a part of the game. The restraint processing unit 12*d* may reproduce, for example, a music. In this case, the restraint processing unit 12*d* may guide the user U to sing by estimating a favorite song of the user U based on the user information 11*b* and reproducing it.

As illustrated in FIG. 16, the restraint processing unit 12*d* guides the user U, for example, to induce drowsiness by sounds and images. VR sickness of the user U can be reduced by inducing drowsiness.

As illustrated in FIG. 16, the restraint processing unit 12*d* may guide a behavior of the user U not only by sounds and images but also by a vibration generated by a vibration presenting device described hereinbefore. In a case of guiding by using a vibration, the restraint processing unit 12*d* may give a vibration that causes a prick pain to a part of the body of the user U so as to guide a head of the user U to look at a direction toward the part, cause the user U to change his/her posture, or distract the user U under a VR sickness state.

As illustrated in FIG. 17, the restraining process information 11*d* of the third embodiment defines a restraining process to be executed by the restraint processing unit 12*d* in accordance with an extent of VR sickness, namely, a sound guidance process and an image guidance process in the present embodiment. Furthermore, the restraining process information 11*d* can be associated with types of contents as illustrated in FIG. 17.

In the example illustrated in FIG. 17, a degree of sickness gradually increases from L1 up to L3. A content type indicates that sickness is more easily gotten from A up to C. The type in which sickness is easily gotten is, for example, action-oriented, horror-oriented, or the like.

In the example illustrated in FIG. 17, an intensity of the guidance sounds a, b, and c of the sound guidance processes gradually increases (for example, the sound pressure increases) from the guidance sound a up to the guidance sound c. The numeric values 1, 2, and 3 respectively attached to the guidance sounds a, b, and c are indicating that the intensity of the guidance sound gradually increases from 1 to 3. For example, a3 is greater than a2, and a2 is greater than a1 regarding the intensity of the guidance sound a. It's to be noted that each of the guidance sounds includes a vibration.

Processes of the image guidance processes l, m, n, and o are similar to those of the guidance sounds a, b, and c. Accordingly, o is greater than n, n is greater than m, and m is greater than l regarding the relationship for the intensity of the process l, m, n, and o.

Subject to these relationships, in a case of FIG. 17, the restraint processing unit 12*d* executes only the sound guidance process that generates the guidance sound a1 in a case where the type of content is A. In a case where the type of content is B, the restraint processing unit 12*d* executes the process l as the image guidance process as well as the sound guidance process that generates the guidance sound a2 in which its intensity is greater than the guidance sound a1. In a case where the type of content is C, the restraint processing unit 12*d* executes the process m in which its intensity is greater than the process l as the image guidance process as well as the sound guidance process that generates the guidance sound a3 in which its intensity is greater than the guidance sound a2.

If the degree of sickness is L2 and the type of content is A, the restraint processing unit 12*d* executes the process l as the image guidance process as well as the sound guidance process that generates the guidance sound b1 in which its intensity is greater than those of the guidance sounds a1 to a3. In a case where the type of content is B, the restraint processing unit 12*d* executes the process m in which its intensity is greater than that of the process l as the image guidance process as well as the sound guidance process that generates the guidance sound b2 in which its intensity is greater than that of the guidance sound b1. In a case where the type of content is C, the restraint processing unit 12*d* executes, as the image guidance process, the process n in which its intensity is greater than that of the process m as well as the sound guidance process that generates the guidance sound b3 in which its intensity is greater than that of the guidance sound b2.

Similarly, if the type of content is A, the restraint processing unit 12*d* executes the process m as the image guidance process as well as the sound guidance process that generates the guidance sound c1 in which its intensity is greater than those of the guidance sounds b1 to b3. In a case where the type of content is B, the restraint processing unit 12*d* executes, as the image guidance process, the process n in which its intensity is greater than that of the process m as well as the sound guidance process that generates the guidance sound c2 in which its intensity is greater than that of the guidance sound c1. In a case where the type of content is C, the restraint processing unit 12*d* executes, as the image guidance process, the process o in which its intensity is greater than that of the process n as well as the sound guidance process that generates the guidance sound c3 in which its intensity is greater than that of the guidance sound c2.

Returning to explanation of FIG. 14. The restraint processing unit 12*d* executes the restraining process having explained with reference to FIG. 16 and FIG. 17 on the basis of an estimation result of the estimation unit 12*c*, the restraining process information 11*d*, and the guidance information DB 11*e* so as to reflect the above-mentioned execution result on a VR content to be provided to the HMD 3 by the provision unit 12*a*.

Figure 18:
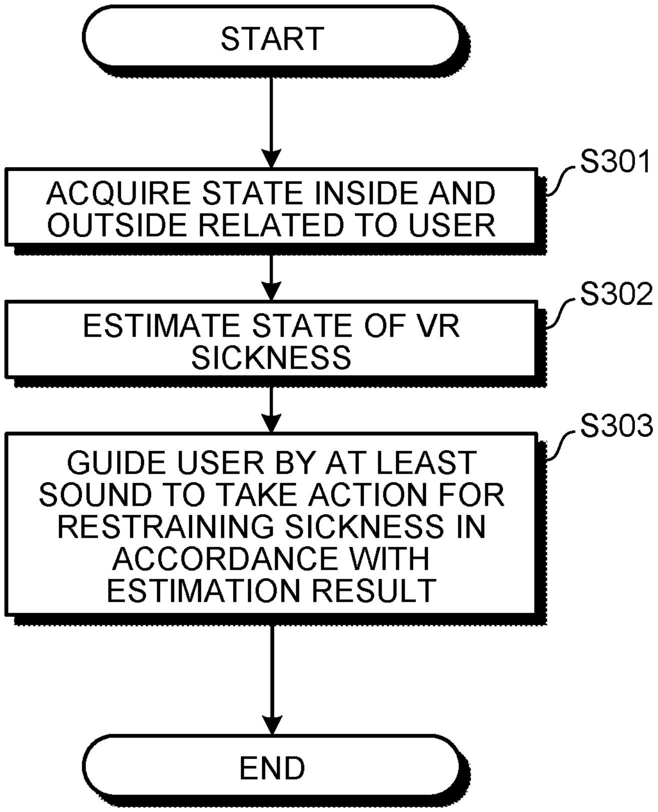
FIG. 18 is a flowchart illustrating a processing procedure to be executed by an information processing device according to the third embodiment.

Next, a processing procedure to be executed by the information processing device 10B according to the third embodiment will be explained with reference to FIG. 18. FIG. 18 is a flowchart illustrating a processing procedure to be executed by the information processing device 10B according to the third embodiment. The processing procedure illustrated in FIG. 18 is repeated at any time during a time interval in which the provision unit 12*a* is providing a VR content to the HMD 3.

As illustrated in FIG. 18, the acquisition unit 12*b* acquires a state inside and outside related to the user U (Step S301). The estimation unit 12*c* estimates a state of VR sickness of the user U on the basis of the acquired state (Step S302).

The restraint processing unit 12*d* guides the user U by at least sounds to take an action for restraining VR sickness in accordance with the estimated estimation result (Step S303). Subsequently, the processing is ended.

As described above, the information processing device 10B according to the third embodiment includes the acquisition unit 12*b*, the estimation unit 12*c*, and the restraint processing unit 12*d*. The acquisition unit 12*b* acquires a state inside and outside related to the user U of a VR content (corresponding to one example of "digital content that includes virtual space experience"). The estimation unit 12*c* estimates a state of VR sickness (corresponding to one example of "sickness") of the user U based on the state that is acquired by the acquisition unit 12*b*. The restraint processing unit 12*d* executes a restraining process of VR sickness for urging the user U to take a behavior that reduces his/her VR sickness, in accordance with the state of VR sickness of the user U that is estimated by the estimation unit 12*c*.

Therefore, in accordance with the information processing device 10B according to the third embodiment, it is possible to restrict VR sickness of the user U due to a VR content. Particularly, in a case of an on-vehicle system like the information processing system 1B according to the third embodiment, it is possible to restrict VR sickness that is caused by deviation of sense that is easy to be caused by a sudden change of a behavior of the vehicle under the state that the user U is not prepared physically or mentally.

The restraint processing unit 12*d* generates a guidance sound that urges the user U to move his/her gaze into a direction in which a tremor is hardly perceived.

Therefore, in accordance with the information processing device 10B according to the third embodiment, it is possible to restrict VR sickness of the user U by guiding the user U to move his/her gaze into a direction in which a vibration or shaking is hardly perceived and urging the user U to change the direction of his/her head portion.

The restraint processing unit 12*d* generates a guidance sound that urges the user U to move his/her gaze into a direction in which fluctuation in an image of the VR content is small.

Therefore, in accordance with the information processing device 10B according to the third embodiment, it is possible to restrict VR sickness of the user U by guiding the user U to move his/her gaze into a distant place in which a stimulation is smaller and urging the user U to change the direction of his/her head portion.

The restraint processing unit 12*d* generates a guidance sound that urges the user U to take a posture in which the user U hardly gets sickness.

Therefore, in accordance with the information processing device 10B according to the third embodiment, it is possible to restrict VR sickness of the user U by guiding the user U to take a posture in such a manner that the vibration perceived at a curve or the like becomes small as possible.

In a case where the user U is an occupant of a vehicle (corresponding to one example of "moving body"), the restraint processing unit 12*d* outputs an alarm sound with respect to an estimated behavior of the vehicle.

Therefore, in accordance with the information processing device 10B according to the third embodiment, it is possible to restrict VR sickness of the user U by making the user U prepare in advance physically and mentally for an influence to be received from the estimated behavior of his/her surroundings.

The restraint processing unit 12*d* generates a guidance sound that urges the user U to utter.

Therefore, in accordance with the information processing device 10B according to the third embodiment, it is possible to restrict VR sickness of the user U by making the user U utter so as to distract the user U.

The restraint processing unit 12*d* generates a guidance sound that induces a drowsiness of the user U.

Therefore, in accordance with the information processing device 10B according to the third embodiment, it is possible to restrict VR sickness of the user U by inducing the drowsiness so as to make the user U relaxed.

The restraint processing unit 12*d* further urges the user U to take a behavior that reduces his/her sickness by using an image and a vibration.

Therefore, in accordance with the information processing device 10B according to the third embodiment, it is possible to guide the user U to effectively take an action to restrict VR sickness by appropriately combining images and vibrations with sounds.

In the above-mentioned embodiments, cases are exemplified in which the HMD 3, the information processing devices 10, 10A, and 10B are separated; however, not limited thereto, they can be integrated together.

In the above-mentioned embodiments, the HMD 3 is explained as a presenting device for presenting VR contents provided by the information processing devices 10, 10A, and 10B; however, not limited thereto, the presenting device may include the above described bone conduction speaker, a vibration presenting device that generates a vibration such as the body-sonic, or the like The presenting device is not limited to a wearable computer; however, in a case of a vehicle, may be a device obtained by configuring a windshield and/or a side window by using a display so as to output an image to the display. Outputting of a sound may be executed by an on-vehicle speaker. In general, the plurality of on-vehicle speakers can be appropriately arranged at locations in many directions including front, rear, left and right, and thus is suitable for the 3D reproduction. For applications other than a vehicle, a wall of a provided space for providing VR content may be configured by using a display, and a plurality of speakers may be arranged in the above-mentioned space similarly to on-vehicle speakers.

In the above-mentioned embodiments, cases are exemplified in which each of the information processing devices 10, 10A, and 10B is configured to provide a VR content; however, it is sufficient that the VR content includes virtual space experience, and may be an Augmented Reality content (AR content), an MR content, or the like.

In the above-mentioned embodiments, cases are exemplified in which each of the information processing devices 10, 10A, and 10B is an on-vehicle device provided in a vehicle; however, not limited thereto, may be a computer such as a game machine configured to provide a digital content including virtual space experience.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

REFERENCE SIGNS LIST

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. An information processing device for a digital content including virtual space experience, the information processing device comprising at least one of a central processing unit, a micro processing unit, and an integrated circuit configured to:

acquire a state inside and outside related to a user of a digital content;

estimate a state of sickness of the user based on the state that is acquired;

execute a restraining process of sickness related to a sound of the digital content in accordance with the state of sickness of the user that is estimated;

execute a restraining process related to an image of the digital content in accordance with the state of sickness of the user that is estimated; and execute balance adjustment between the restraining process related to the sound and the restraining process related to the image in accordance with the state of sickness of the user.

2. The information processing device according to claim 1, wherein the at least one of the central processing unit, the micro processing unit, and the integrated circuit is further configured to:

execute, as the restraining process, a reducing process of sound image localization feeling in the sound of the digital content.

3. The information processing device according to claim 1, wherein the at least one of the central processing unit, the micro processing unit, and the integrated circuit is further configured to execute processes of:

execute, as the restraining process, a reducing process of a sound-volume changing speed in the sound of the digital content.

4. The information processing device according to claim 1, wherein the at least one of the central processing unit, the micro processing unit, and the integrated circuit is further configured to execute processes of:

execute, as the restraining process, a restricting process of a volume changing width in the sound of the digital content.

5. An information processing device for a digital content including virtual space experience, the information processing device comprising at least one of a central processing unit, a micro processing unit, and an integrated circuit configured to:

acquire a state inside and outside related to a user of a digital content;

estimate a state of sickness of the user based on the state that is acquired;

execute a restraining process of sickness related to a sound of the digital content in accordance with the state of sickness of the user that is estimated; and execute a restraining process of sickness for urging the user by using a sound to take a behavior that reduces his/her sickness, in accordance with the state of sickness of the user that is estimated.

6. An information processing device for a digital content including virtual space experience, the information processing device comprising at least one of a central processing unit, a micro processing unit, and an integrated circuit configured to:

acquire a state inside and outside related to a user of a digital content;

estimate a state of sickness of the user based on the state that is acquired;

execute a restraining process of sickness related to at least one of a sound or an image of the digital content in accordance with the state of sickness of the user that is estimated; and when executing the restraining process, execute a balance adjustment between the restraining process related to the sound and the restraining process related to the image in accordance with the state of sickness of the user.

7. The information processing device according to claim 6, wherein the at least one of the central processing unit, the micro processing unit, and the integrated circuit is further configured to:

where a degree indicating the state of sickness is a light degree, executing the restraining process related to the sound.

8. The information processing device according to claim 6, wherein the at least one of the central processing unit, the micro processing unit, and the integrated circuit is further configured to:

where a degree indicating the state of sickness is a middle extent, executing the restraining process related to the image.

9. The information processing device according to claim 6, wherein the at least one of the central processing unit, the micro processing unit, and the integrated circuit is further configured to:

where a degree indicating the state of sickness is large extent, mainly executing both the restraining process related to the image and the restraining process related to the sound.

10. The information processing device according to claim 6, wherein the at least one of the central processing unit, the micro processing unit, and the integrated circuit is further configured to:

where a degree indicating the state of sickness becomes larger, executing the restraining process related to the sound and then executing the restraining process related to the image.

11. The information processing device according to claim 6, wherein the at least one of the central processing unit, the micro processing unit, and the integrated circuit is further configured to:

change a content of the restraining process related to the sound and a content of the restraining process related to the image in accordance with a degree indicating the state of sickness.

12. An information processing device for a digital content including virtual space experience, the information processing device comprising at least one of a central processing unit, a micro processing unit, and an integrated circuit configured to:

acquire a state inside and outside related to a user of a digital content;

estimate a state of sickness of the user based on the state that is acquired; and execute a restraining process of sickness for urging the user by using a sound to take a behavior that reduces his/her sickness, in accordance with the state of sickness of the user that is estimated.

13. The information processing device according to claim 12, wherein the at least one of the central processing unit, the micro processing unit, and the integrated circuit is further configured to:

generate, as the restraining process, a guidance sound that urges the user to move his/her gaze into a direction in which a tremor is hardly perceived.

14. The information processing device according to claim 12, wherein the at least one of the central processing unit, the micro processing unit, and the integrated circuit is further configured to:

generate, as the restraining process, a guidance sound that urges the user to move his/her gaze into a direction in which fluctuation in an image of the digital content is small.

15. The information processing device according to claim 12, wherein the at least one of the central processing unit, the micro processing unit, and the integrated circuit is further configured to:

generate, as the restraining process, a guidance sound that urges the user to take a posture in which the user hardly gets sickness.

16. The information processing device according to claim 12, wherein the at least one of the central processing unit, the micro processing unit, and the integrated circuit is further configured to:

where the user is an occupant of a moving body, output, as the restraining process, an alarm sound with respect to an estimated behavior of the moving body.

17. The information processing device according to claim 12, wherein the at least one of the central processing unit, the micro processing unit, and the integrated circuit is further configured to:

generate, as the restraining process, a guidance sound that urges the user to utter.

18. The information processing device according to claim 12, wherein the at least one of the central processing unit, the micro processing unit, and the integrated circuit is further configured to:

generate, as the restraining process, a guidance sound that induces a drowsiness of the user.

* * * * *